(12) United States Patent
Suzuki et al.

(10) Patent No.: US 8,300,762 B2
(45) Date of Patent: Oct. 30, 2012

(54) X-RAY CT IMAGING APPARATUS

(75) Inventors: Masakazu Suzuki, Kyoto (JP);
Takahiro Yoshimura, Kyoto (JP);
Makoto Honjo, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 95 days.

(21) Appl. No.: 12/734,656

(22) PCT Filed: Nov. 14, 2008

(86) PCT No.: PCT/JP2008/070760
§ 371 (c)(1),
(2), (4) Date: May 14, 2010

(87) PCT Pub. No.: WO2009/063974
PCT Pub. Date: May 22, 2009

(65) Prior Publication Data
US 2010/0246755 A1    Sep. 30, 2010

(30) Foreign Application Priority Data
Nov. 16, 2007 (JP) ................. 2007-298183

(51) Int. Cl.
*A61B 6/14* (2006.01)
*G01N 23/083* (2006.01)
*H05G 1/60* (2006.01)
*H05G 1/02* (2006.01)
(52) U.S. Cl. ............... 378/39; 378/15; 378/197
(58) Field of Classification Search .......... 378/4–20, 378/38, 39, 193, 195–198, 204, 205, 208, 378/210
See application file for complete search history.

(56) References Cited

U.S. PATENT DOCUMENTS

| 4,501,011 A * | 2/1985 | Hauck et al. ........... 378/196 |
| 5,598,453 A | 1/1997 | Baba et al. |
| 6,118,842 A | 9/2000 | Arai et al. |
| 6,381,299 B1 | 4/2002 | Baba et al. |
| 6,493,415 B1 | 12/2002 | Arai et al. |
| 6,582,121 B2 * | 6/2003 | Crain et al. ........... 378/197 |
| 7,197,109 B2 | 3/2007 | Rotondo et al. |
| 7,269,242 B2 | 9/2007 | Tanaka et al. |
| 7,315,608 B2 | 1/2008 | Sa et al. |
| 7,347,622 B2 | 3/2008 | Sadakane et al. |

(Continued)

FOREIGN PATENT DOCUMENTS
JP    H08-117220 A    5/1996
(Continued)

*Primary Examiner* — Anastasia Midkiff
(74) *Attorney, Agent, or Firm* — DLA Piper LLP (US)

(57) ABSTRACT

In an X-ray CT imaging, an X-ray generator (11) and a two-dimensional X-ray detector (21) are opposed to each other between an object and are rotated by a rotary shaft (32) around the object. At least one of the rotary shaft supporter (61) and an object holder (40) includes a movement mechanism (42, 65) for moving a supporter (30) for the X-ray generator and the X-ray detector relative to the object. In offset scan CT imaging, the rotation of the supporter by the rotary shaft is performed simultaneously with the relative two-dimensional movement of the rotary shaft by the movement mechanism. In the relative two-dimensional movement, the position of the rotary shaft is moved according to the rotary angle of the supporter along a circular orbit around the center of a CT imaging region in a plane crossing the rotary shaft. Thus, it becomes possible to image a larger region of interest of the object.

8 Claims, 29 Drawing Sheets

U.S. PATENT DOCUMENTS

| | | |
|---|---|---|
| 7,486,759 B2 | 2/2009 | Suzuki et al. |
| 2003/0112926 A1* | 6/2003 | Atzinger ................... 378/196 |
| 2003/0235265 A1 | 12/2003 | Clinthorne et al. |
| 2004/0258195 A1 | 12/2004 | Hara |
| 2005/0265523 A1 | 12/2005 | Strobel |
| 2007/0041491 A1 | 2/2007 | Sadakane et al. |
| 2007/0268994 A1* | 11/2007 | Chen ............................ 378/4 |
| 2008/0317216 A1* | 12/2008 | Lifshitz et al. ............. 378/209 |
| 2009/0041191 A1 | 2/2009 | Suzuki et al. |

FOREIGN PATENT DOCUMENTS

| | | | |
|---|---|---|---|
| JP | H09-164133 A | | 6/1997 |
| JP | H09-327453 A | | 12/1997 |
| JP | H10-225455 A | | 8/1998 |
| JP | H11-9583 A | | 1/1999 |
| JP | H11-226004 A | | 8/1999 |
| JP | 2002-204796 A | | 7/2002 |
| JP | 2002-219127 A | | 8/2002 |
| JP | 2004-45212 A | | 2/2004 |
| JP | 3540916 B | | 4/2004 |
| JP | 2005-6772 A | | 1/2005 |
| JP | 2006-34670 A | | 2/2006 |
| JP | 2007-29168 A | | 2/2007 |
| JP | 2007-143948 A | | 6/2007 |
| JP | 2007-159987 A | | 8/2007 |
| JP | 2008-114056 A | | 5/2008 |
| WO | WO 99/27857 A | | 6/1999 |
| WO | WO 2006/013325 A | | 2/2006 |
| WO | WO 2006/109808 A | | 10/2006 |
| WO | WO 2008040356 A1 * | | 4/2008 |

* cited by examiner

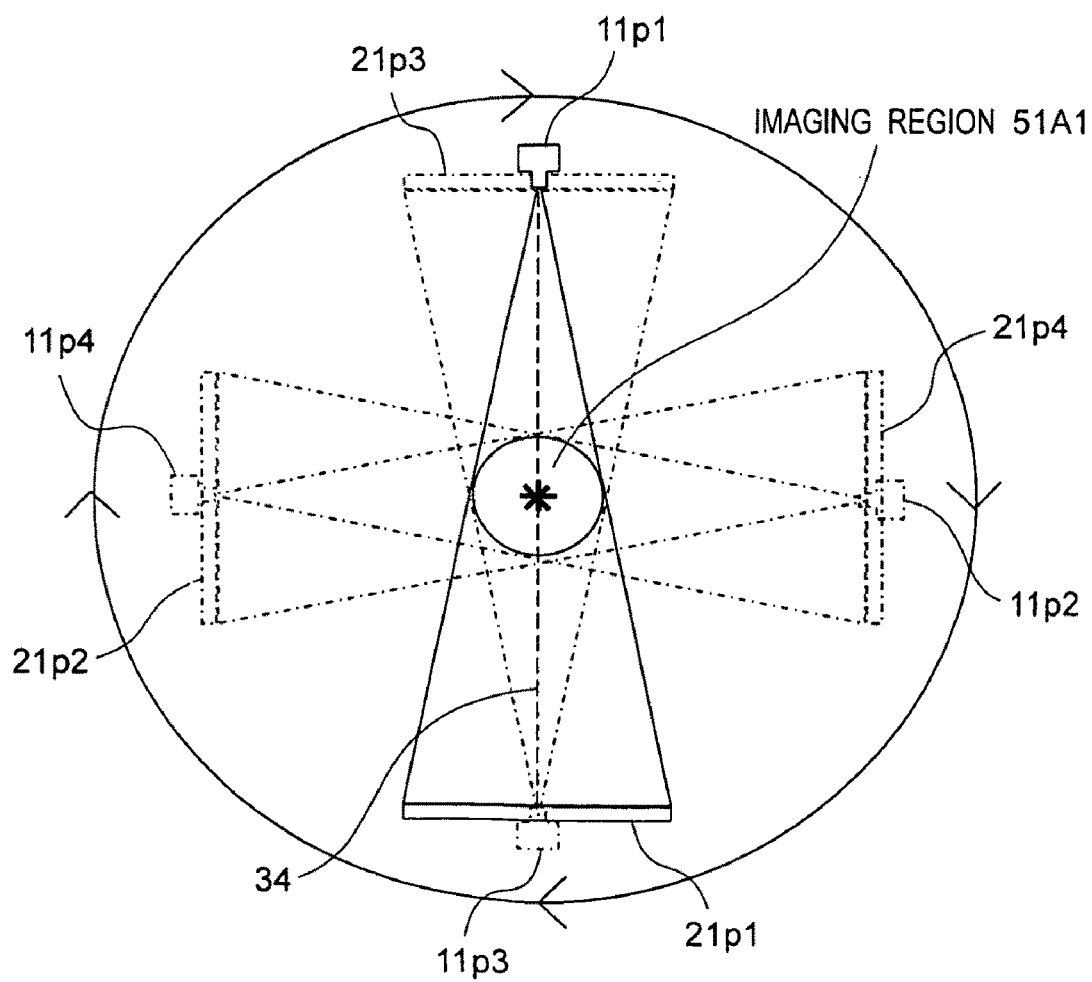

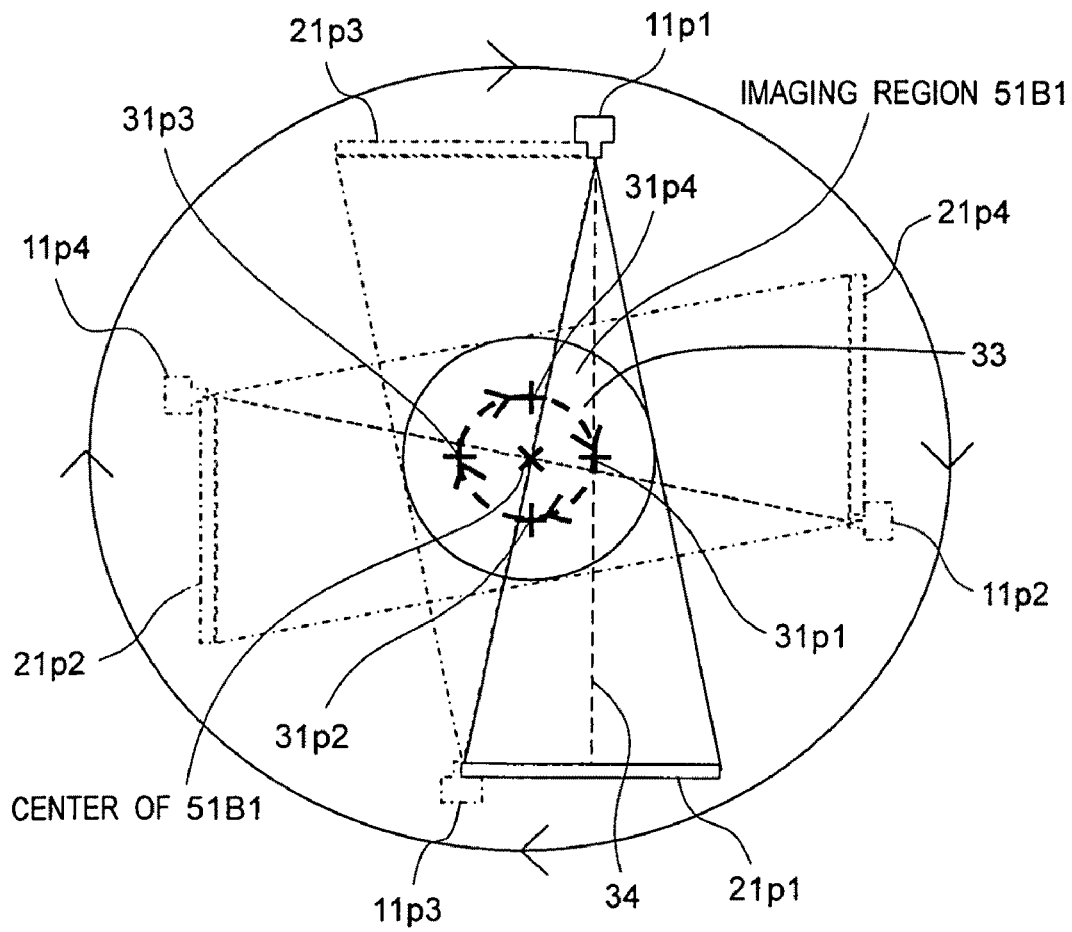

POSITION OF X-RAY DETECTOR : 21p1→21p2→21p3→21p4→21p1
CENTER OF REVOLUTION +( + ) : 31p1→31p2→31p3→31p4→31p1
(CIRCULAR MOVEMENT)
CENTER POSITION OF IMAGING REGION ×( × ) : FIXED

Fig.4A
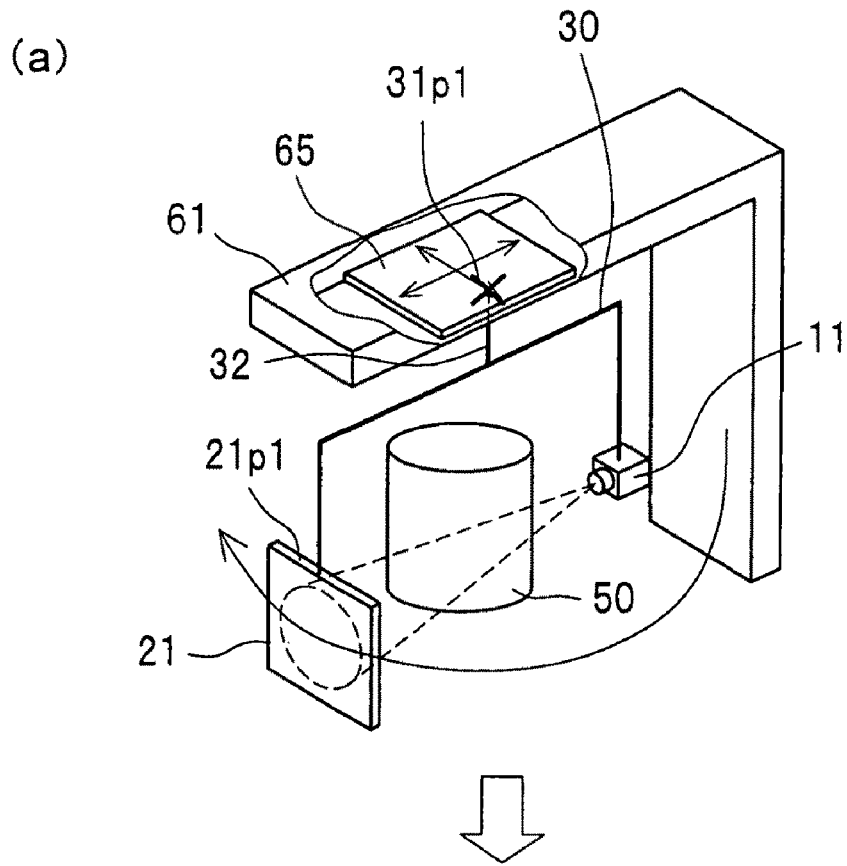
(a)
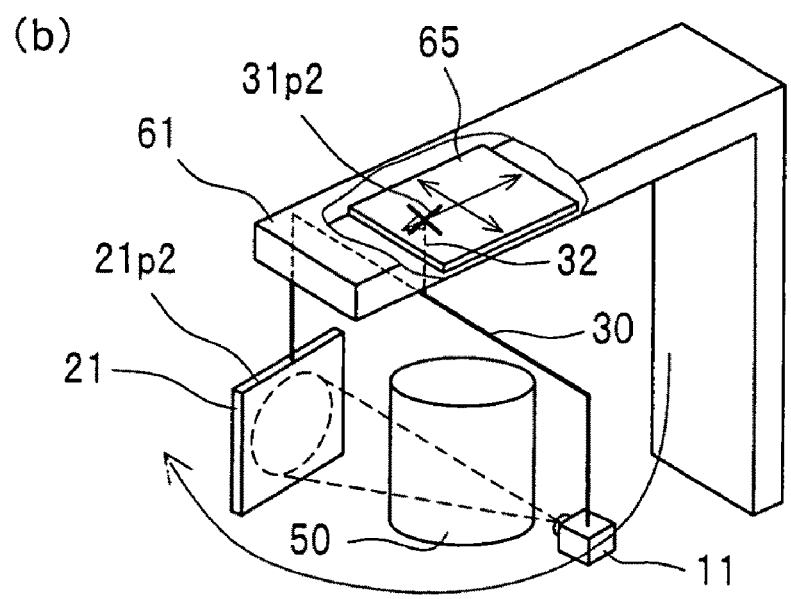
(b)

Fig.4B
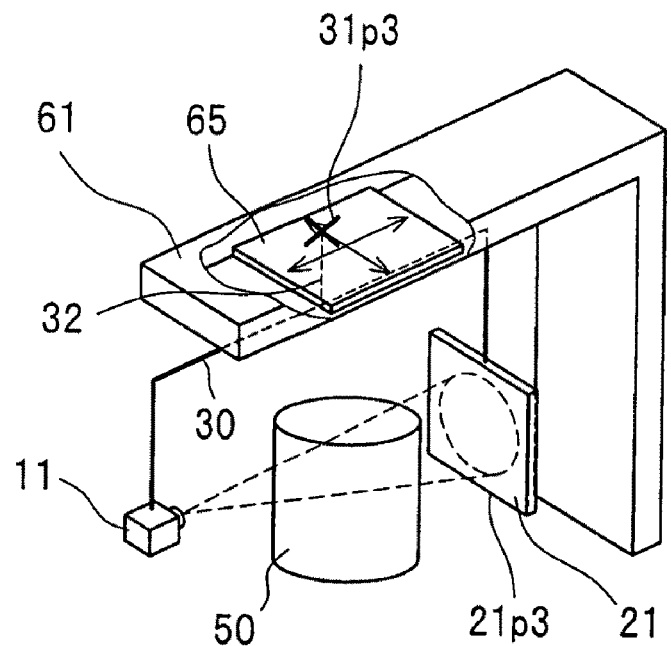
(c)
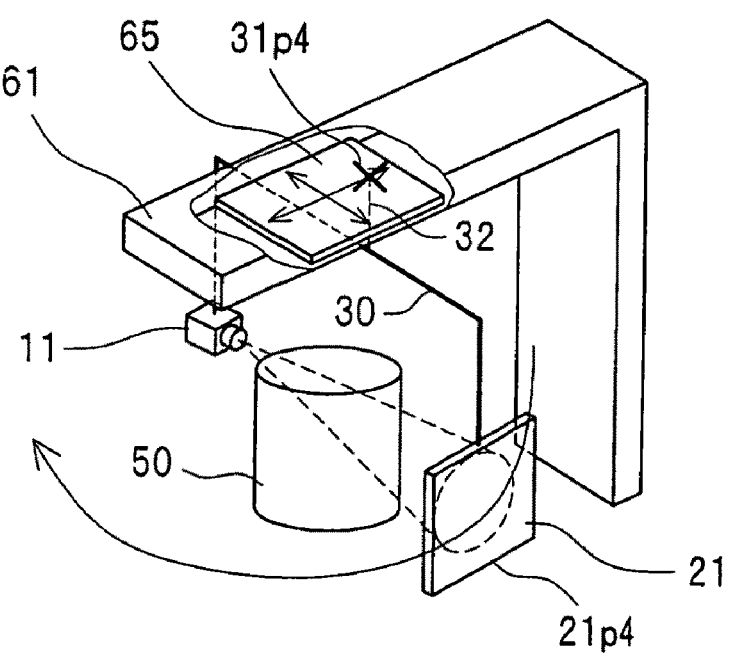
(d)

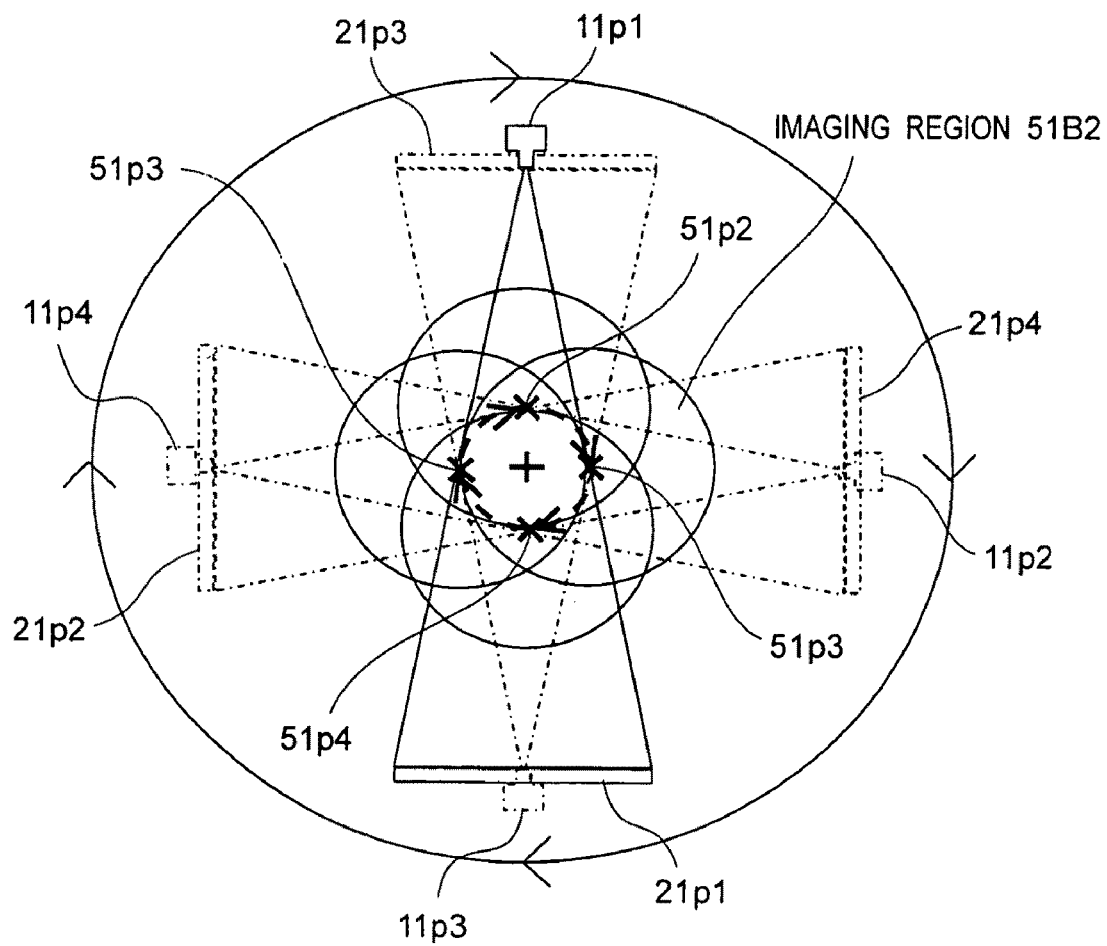

POSITION OF X-RAY DETECTOR : 21p1→21p2→21p3→21p4→21p1

CENTER POSITION OF IMAGING REGION × ( ✕ ) : 51p1→51p2→51p3→51p4→51p5
(CIRCULAR MOVEMENT)

Fig.6A
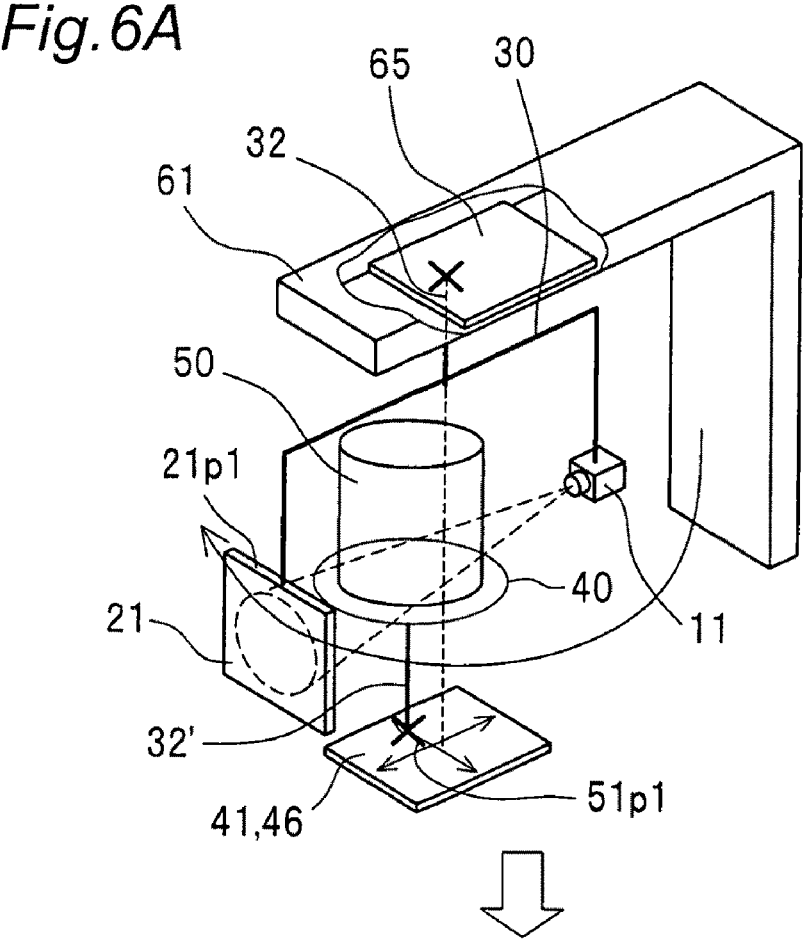
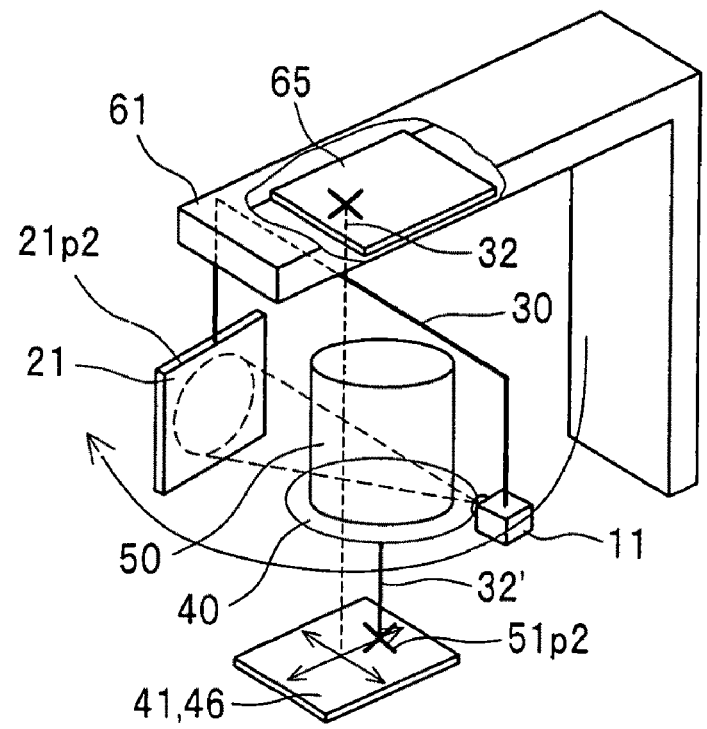

Fig.6B
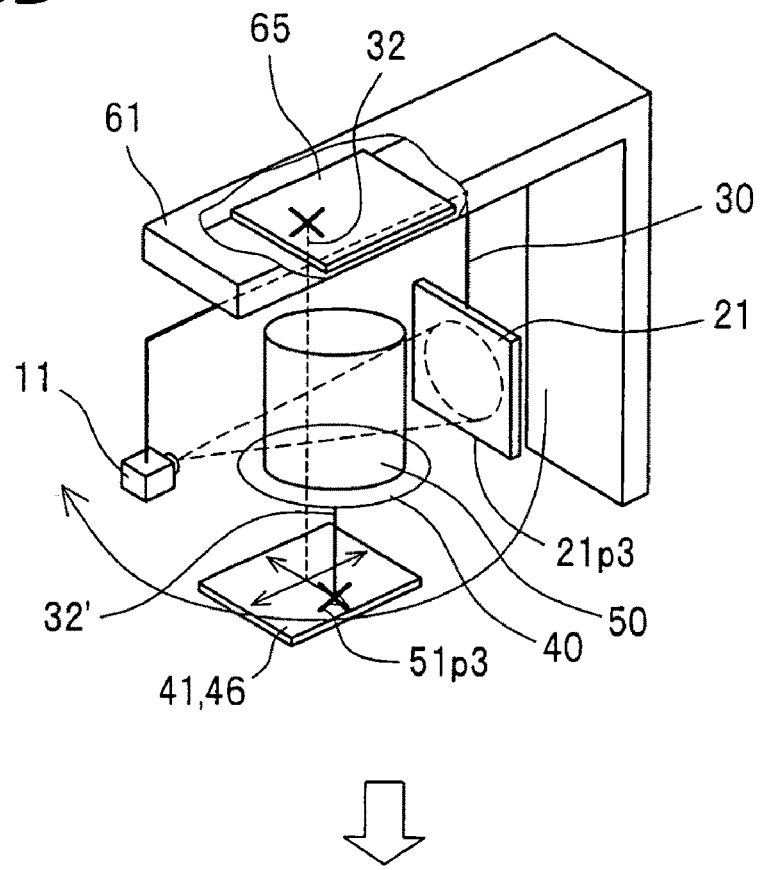
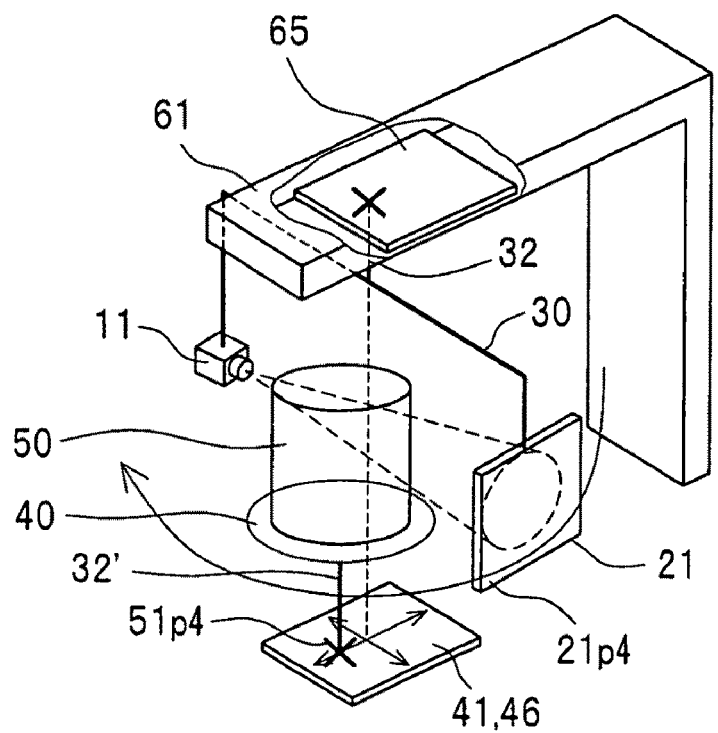

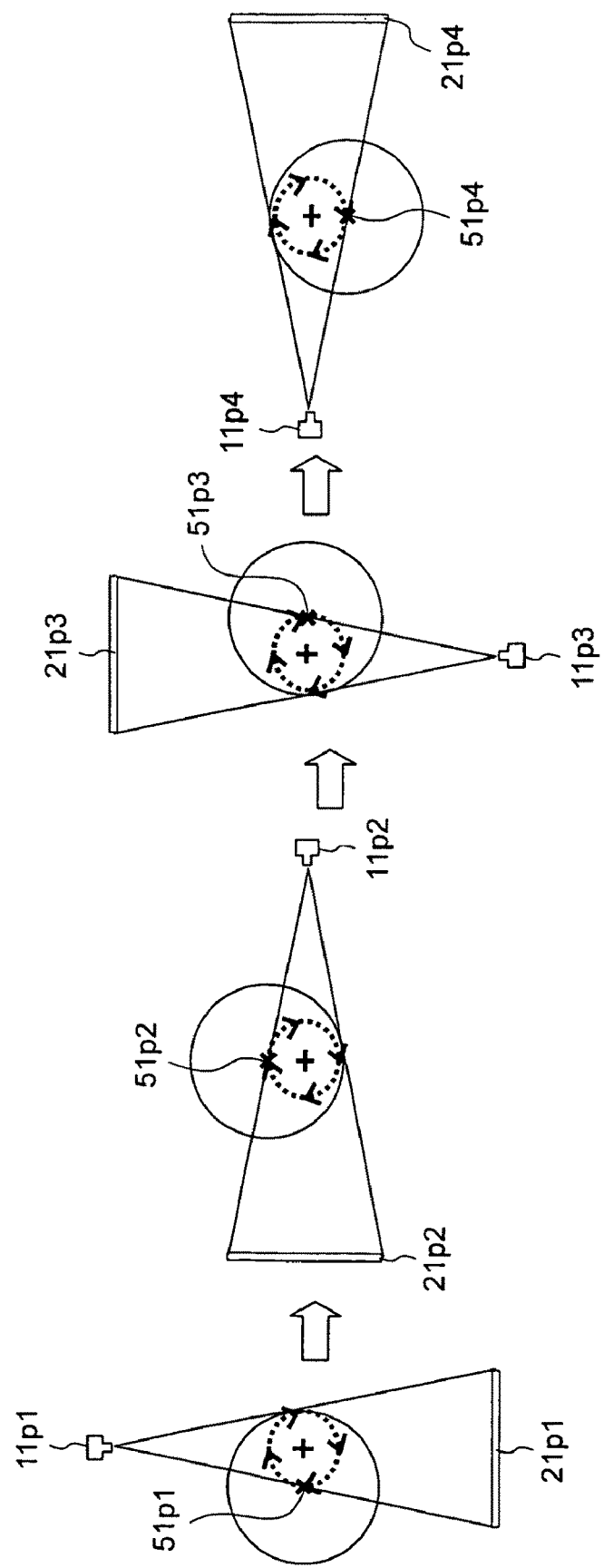

POSITION OF X-RAY DETECTOR : 21p1→21p2→21p3→21p4→21p1

CENTER POSITION OF REVOLUTION ( + ) : 31p1'→31p2'→31p3'→31p4'→31p1'
(LINEAR MOVEMENT)

CENTER POSITION OF IMAGING REGION × ( ✕ ) : 51p1'→51p2'→51p3'→51p4'→51p1'
(LINEAR MOVEMENT)

POSITION OF X-RAY DETECTOR : 21p1→21p2→21p3→21p4→21p1

CENTER POSITION OF REVOLUTION ( + ) : 31p1'→31p2'→31p3'→31p4'→31p1'
(LINEAR MOVEMENT)

Fig.10A
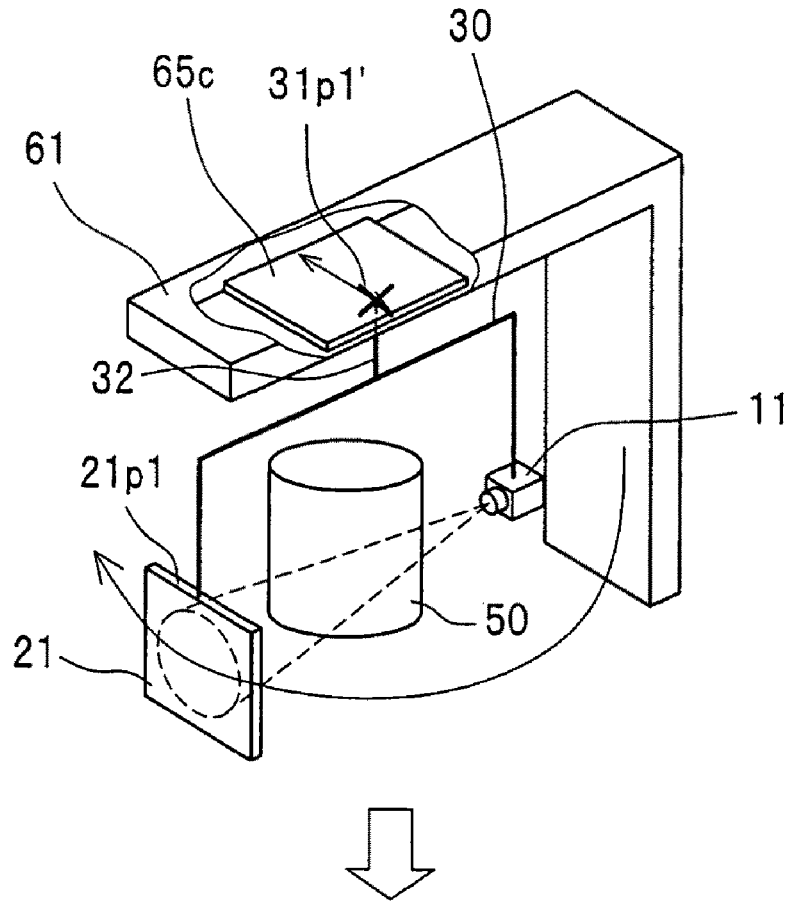
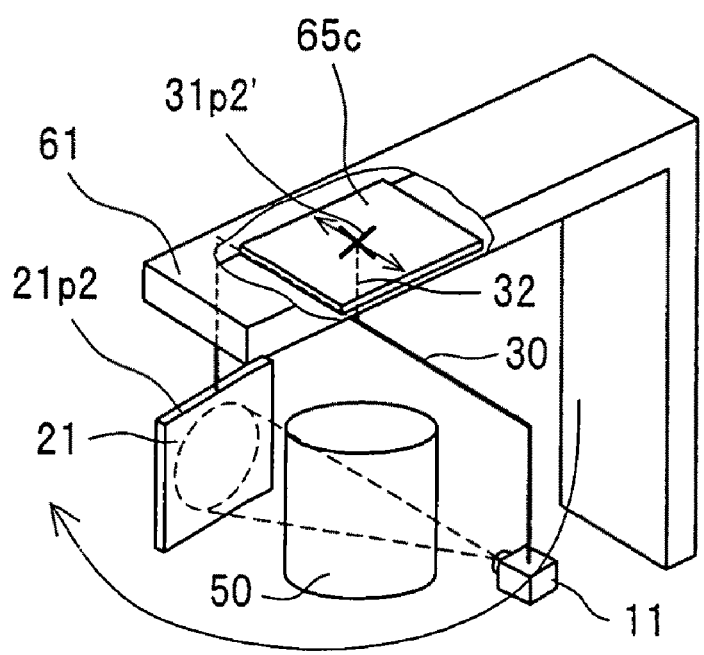

Fig.10B
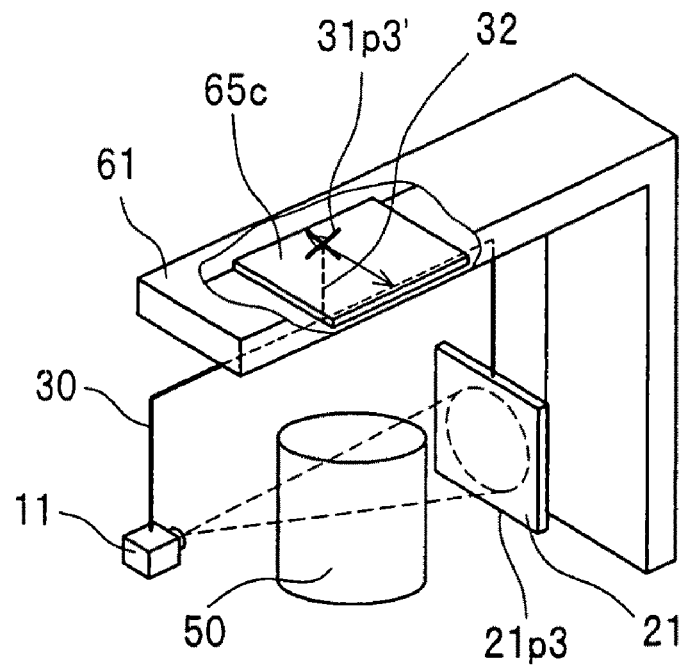
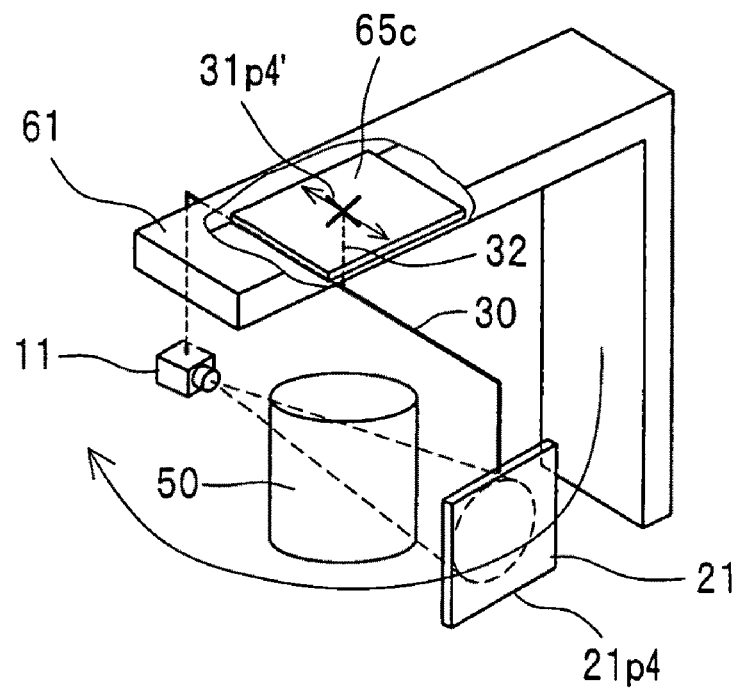

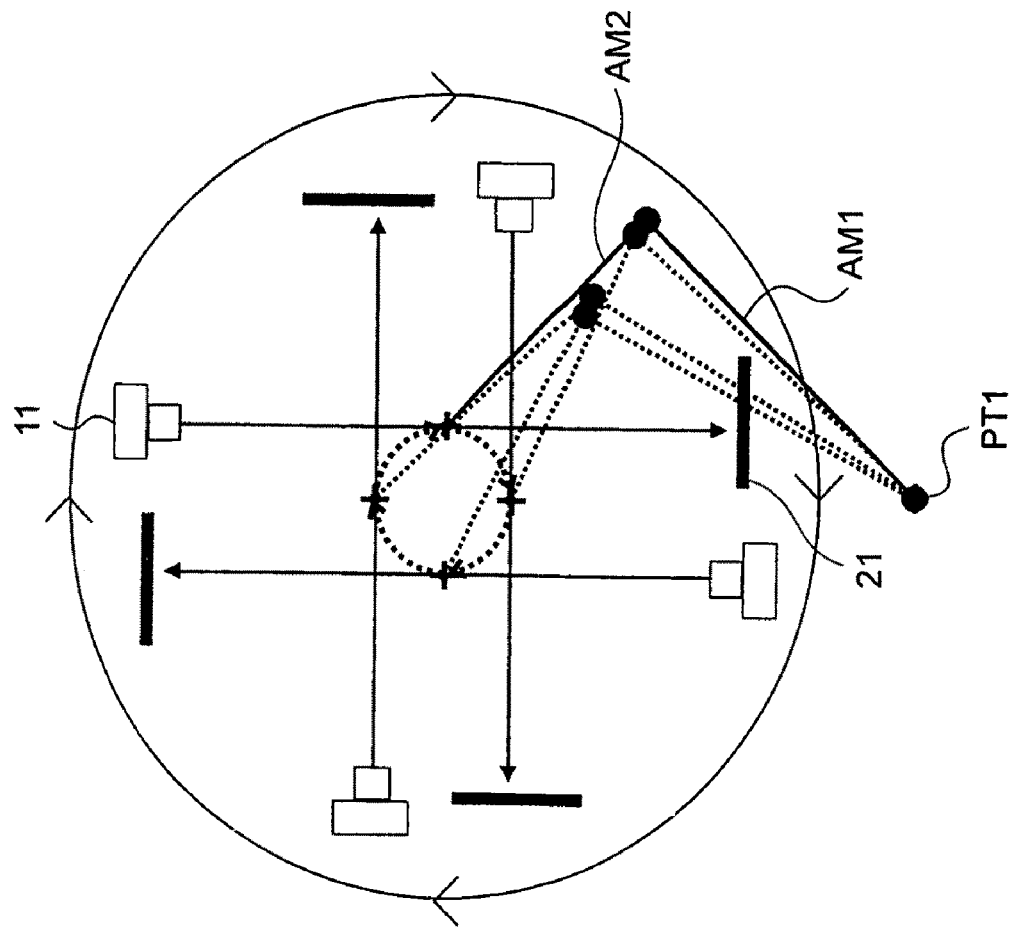
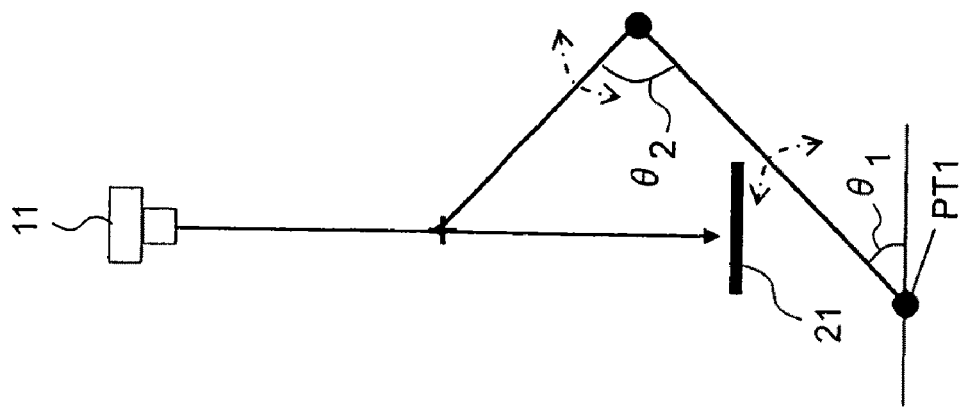
Fig.18

Fig.19
(a)
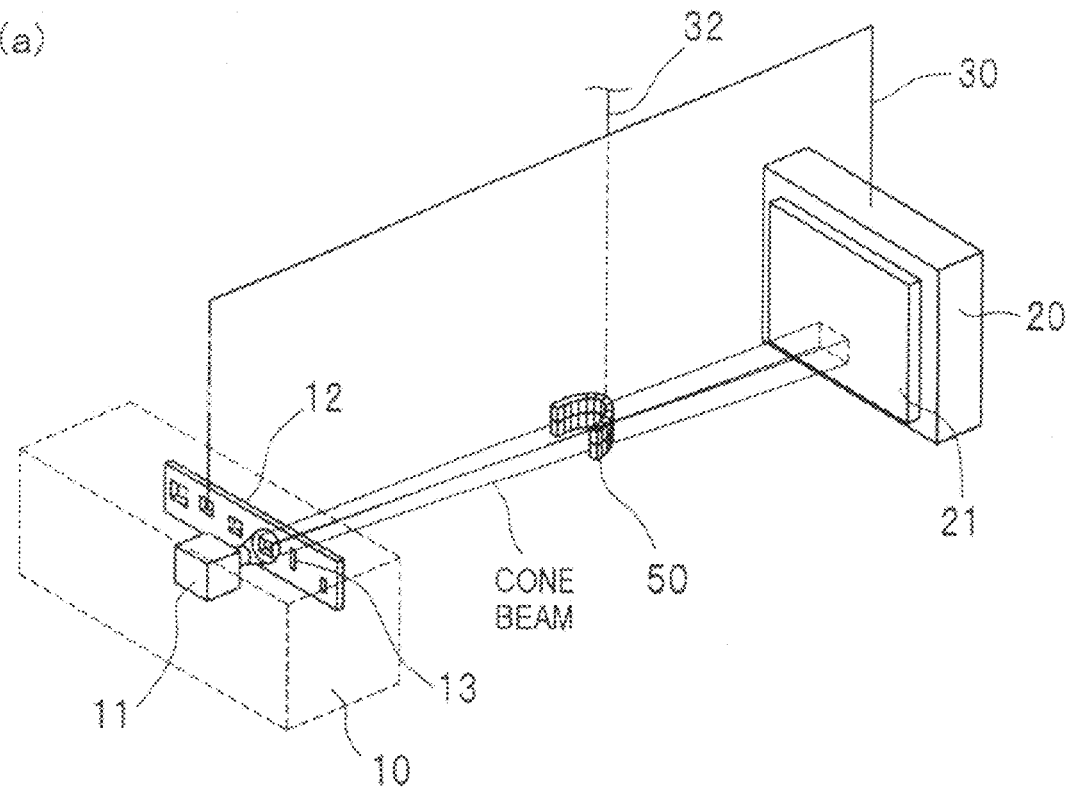
(b)
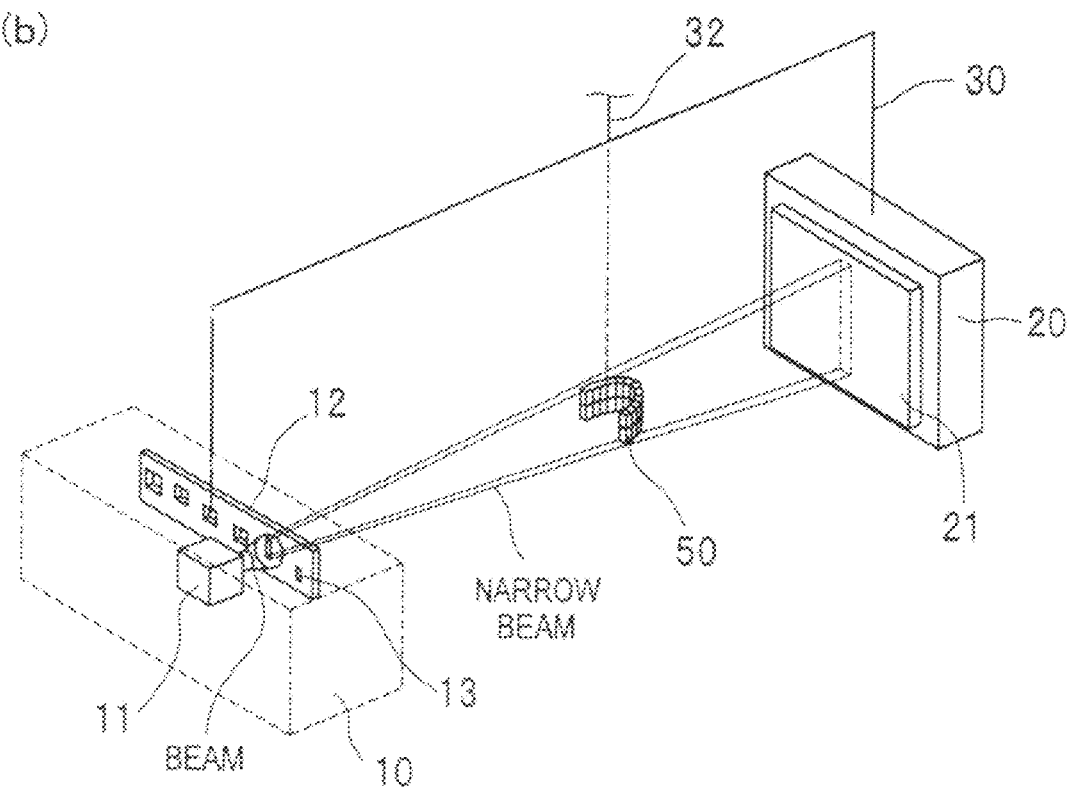

X-RAY CT IMAGING APPARATUS

TECHNICAL FIELD

The invention relates to an X-ray computerized tomography (CT) imaging apparatus, in particular, a head X-ray CT imaging apparatus using an X-ray cone beam, suitable for dentistry, oral surgery, opthalmology, otolaryngology and the like.

BACKGROUND ART

In an X-ray computer tomography apparatus using an X-ray cone beam, an X-ray generator and an X-ray detector interposing an object is rotated around the object relative to the object. During the rotation, the X-ray generator generates an X-ray cone beam having a cone or pyramid shape to irradiate the object in various directions, and the X-ray detector having a two-dimensional detection plane measures an intensity distribution of X-rays transmitting the object or a projection of the object. The acquired projection data is back-projected to reconstruct the distribution of X-ray absorption coefficients and to create a two-dimensional tomographic view or a three-dimensional stereoscopic view.

An X-ray detector for a wider imaging area is generally more expensive. Therefore, it is proposed to image a wider area with a less-expensive X-ray detector having a smaller detection area. In a normal X-ray cone beam CT imaging the entire imaging area is always included in an X-ray irradiation field, and the projection in the entire imaging area is detected. The image reconstruction can be carried out by using projection data obtained during a rotation of 180 degrees. On the other hand, X-ray cone-beam CT imaging apparatuses described in JP-A 2002-204796 and 2005-6772 shift detection center in the X-ray detector in a direction perpendicular to a line connecting the X-ray detector and an axis of the object (or rotation center) for CT imaging. When the shift becomes larger, the X-ray detector detects, in each instant, not the entire area to be imaged, but a part thereof. However, by using projection data obtained during a rotation of 360 degrees, an image of an area wider by the offset of the detection center can be reconstructed. If the position of the X-ray detector is shifted so that the line connecting the X-ray detector and the rotation center reaches to an edge of the detection plane, the X-ray detector detects, in each instant, the X-rays transmitting a half of the area of interest to be imaged, while the width of the imaged area during the rotation of 360 degrees become twice in contrast to the normal CT imaging.

In an X-ray CT imaging apparatus described in JP-A 2007-29168, a distance between an X-ray generator (and/or an X-ray detector) and the revolution center is changed relatively in order to change the magnification factor. Because the revolution center of the X-ray generator and the X-ray detector is different from the center of a region of interest in an object, the positions of the X-ray generator and the X-ray detector are controlled so that the relative position relationship between the X-ray generator, the object and the X-ray detector is kept constant. In a X-ray cone-beam CT imaging apparatus described in JP-A 2007-143948, one rotation driver can be used for CT and panorama imaging. However, CT imaging with an offset scan cannot be performed. In the apparatus, the rotary arm is set below a patient. Further, In an X-ray cone-beam CT imaging apparatus described in JP-A H09-327453, an X-ray tube and an X-ray image intensifier (X-ray detector) are mounted opposing to each other in a gantry, and they can be moved in the gantry along an arc. Thus, the field of view of a tomographic section in an X-ray CT image can be enlarged. However, the apparatus cannot perform panorama imaging.

As explained above, the size of a reconstructed image can be changed largely by shifting the position of the X-ray generator relatively to that for the normal CT imaging. However, it is desirable to image a still larger region of interest of an object.

DISCLOSURE OF THE INVENTION

Problem to be Solved

It is a problem of the invention to image a still larger region of interest of an object.

Solutions

A first X-ray CT imaging apparatus according to the invention includes a first supporter for supporting an X-ray generator generating an X-ray cone beam and a two-dimensional X-ray detector, the X-ray generator and the X-ray detector being arranged to interpose an object, a rotary shaft for revolving the supporter around the object, and a second supporter supporting the rotary shaft. At least one of the second supporter and an object holder for holding the object has a movement mechanism for moving the first supporter relative to the object. In CT imaging with offset scan, the revolution of the supporter by the rotary shaft is performed at the same time as relative two-dimensional displacement of the rotary shaft by the movement mechanism. In the relative two-dimensional movement of the rotary shaft, a position of the rotary shaft is moved according to a rotary angle of the first supporter in two dimensions in a plane crossing the rotary shaft along a circular orbit around a center of a CT imaging region (offset from the center of the CT imaging region).

A second X-ray CT imaging apparatus according to the invention includes a first supporter for supporting an X-ray generator generating an X-ray cone beam and a two-dimensional X-ray detector, the X-ray generator and the X-ray detector being arranged to interpose an object, a rotary shaft for revolving the first supporter around the object; and a second supporter supporting the rotary shaft. At least one of the second supporter and an object holder for holding the object has a movement mechanism for moving the first supporter relative to the object. In a CT imaging with offset scan, the revolution of the supporter by the rotary shaft is performed at the same time as relative two-dimensional movement of the rotary shaft by the movement mechanism. In the relative two-dimensional movement of the rotary shaft, a position of the rotary shaft is moved along a circular orbit in a plane intersecting the rotary shaft, and a center of revolution of the X-ray cone beam around the object according to the rotation of the supporter is set to a position different from a symmetrical axis of the broadening X-ray cone beam.

A third X-ray CT imaging apparatus according to the invention includes a first supporter for supporting an X-ray generator generating an X-ray cone beam and a two-dimensional X-ray detector, the X-ray generator and the X-ray detector being arranged to interpose an object; a rotary shaft for revolving the supporter around the object; a second supporter supporting the rotary shaft; and a mode changer for changing between normal CT imaging mode and offset CT imaging mode. At least one of the second supporter and an object holder for holding the object has a movement mechanism for moving the first supporter relative to the object. In the normal CT imaging mode, the position of the rotary shaft is fixed at a center of a region to be imaged in a plane perpendicular to the rotary shaft, and the first supporter is revolved. In the offset CT imaging mode, the revolution of the first supporter by the rotary shaft is performed at the same time as relative two-dimensional movement of the rotary shaft by the movement mechanism, and in the relative two-dimensional movement of the rotary shaft, a position of the rotary shaft is moved along a circular orbit, and a revolution center of the X-ray cone beam around the object according to the rotation of the first supporter is set to a position different from a symmetrical axis of the broadening X-ray cone beam (offset from the center of the CT imaging region).

In any of the X-ray CT imaging apparatuses, for example, a displacement device is provided in the supporter, and it displaces the rotary shaft held by a supporting frame relative to the center axis of the imaging region.

In any of the X-ray CT imaging apparatuses, for example, the displacement device has a first moving device mounted to the supporting frame and displacing the rotary shaft in a plane crossing the center axis so as to move the center axis in the first direction, and a second moving device mounted to the object holder and displacing the object in the second direction different from the first direction. In CT imaging, the simultaneous displacement of the center axis in the first direction and the object in the second direction creates a synthesized motion, to move the center axis while keeping the center of the irradiated region at the center of a circular orbit.

In any of the X-ray CT imaging apparatuses, for example, the circular orbit is a true circle.

In any of the X-ray CT imaging apparatuses, for example, the movement mechanism is set in the second supporter or in the object holder.

In any of the X-ray CT imaging apparatuses, for example, the movement mechanism includes a first part in the second supporter for moving the position of the rotary shaft along a first direction in a plane crossing the rotary shaft, and a second part in the object holder for moving the position of the rotary shaft in a second direction different from the first direction.

Any of the X-ray CT imaging apparatuses, for example, has a device for restricting an irradiation field, wherein the device restricts the X-ray beam generated by the X-ray generator to a narrow width beam having a width narrower in an axial direction of the rotary shaft than in a direction in parallel to the axial direction, and at least one of panorama imaging and cephalometric X-ray imaging is possible by irradiating the narrow width beam.

Advantages of The Invention

In an X-ray imaging apparatus of the invention, because an X-ray cone beam irradiating a part of a region of an object to be imaged is incident onto the X-ray detector, the region to be imaged can be enlarged, in contrast to a case wherein the X-ray transmitting the entire region of interest is incident onto the X-ray detector. Further, because the rotary shaft is moved relative to the center of the region to be imaged, the magnifying factor of the reconstructed image can be changed. Thus, CT imaging can be performed in a larger region of interest. For example, if the supporter is revolved while shifted relative to the rotary shaft, CT imaging can be performed in a larger region of interest. Further, the X-ray generator and the object are moved around the object while moving the rotary shaft and the object, CT imaging can be performed in a larger region of interest. If the supporter is rotated while the object is fixed, CT imaging can be performed in a larger region of interest.

In the X-ray imaging apparatus, for example, CT imaging can be performed in a larger region of interest by rotating the center position of the rotary shaft of the supporter relative to a region to be imaged along a circular orbit having a center in a region of interest while rotating the supporter.

In the X-ray imaging apparatus, for example, the rotary shaft or the object can be moved in a plane by moving the rotary shaft or the object in the first and second directions.

In the X-ray imaging apparatus, preferably, an X-ray narrow beam can be irradiated so that at least one of panorama imaging and cephalometric X-ray imaging becomes possible.

BRIEF DESCRIPTION OF THE DRAWINGS

FIG. 1 is a diagram for explaining position relationship between an X-ray generator, an X-ray detector and an object in a normal X-ray CT imaging.

FIG. 2A is a diagram for explaining position relationship between an X-ray generator, an X-ray detector, an object and a rotary shaft at four phases in an embodiment of the invention.

FIG. 4A is a schematic diagram at two positions shown in FIGS. 2A and 2B.

FIG. 4B is a schematic diagram at the other two positions shown in FIGS. 2A and 2B.

FIG. 5A is a diagram of explaining a position relationship between the X-ray generator, the X-ray detector, the object and a rotary shaft at four phases in an embodiment of the invention.

FIG. 6A is a schematic diagram at two positions shown in FIGS. 5A and 5B.

FIG. 6B is a schematic diagram at the other two positions shown in FIGS. 5A and 5B.

FIG. 7 is a sectional view at the four positions shown in FIGS. 5A and 5B.

FIG. 10A is a schematic diagram at two positions in the embodiment shown in FIG. 9.

FIG. 10B is a schematic diagram at the other two positions in the embodiment shown in FIG. 9.

FIG. 18 is a diagram of a structure of a modified example of a rotary system.

FIG. 19 is a diagram for explaining a double-purpose apparatus used for CT and panorama imaging.

EXPLANATION OF REFERENCE SYMBOLS

Figure 2B:
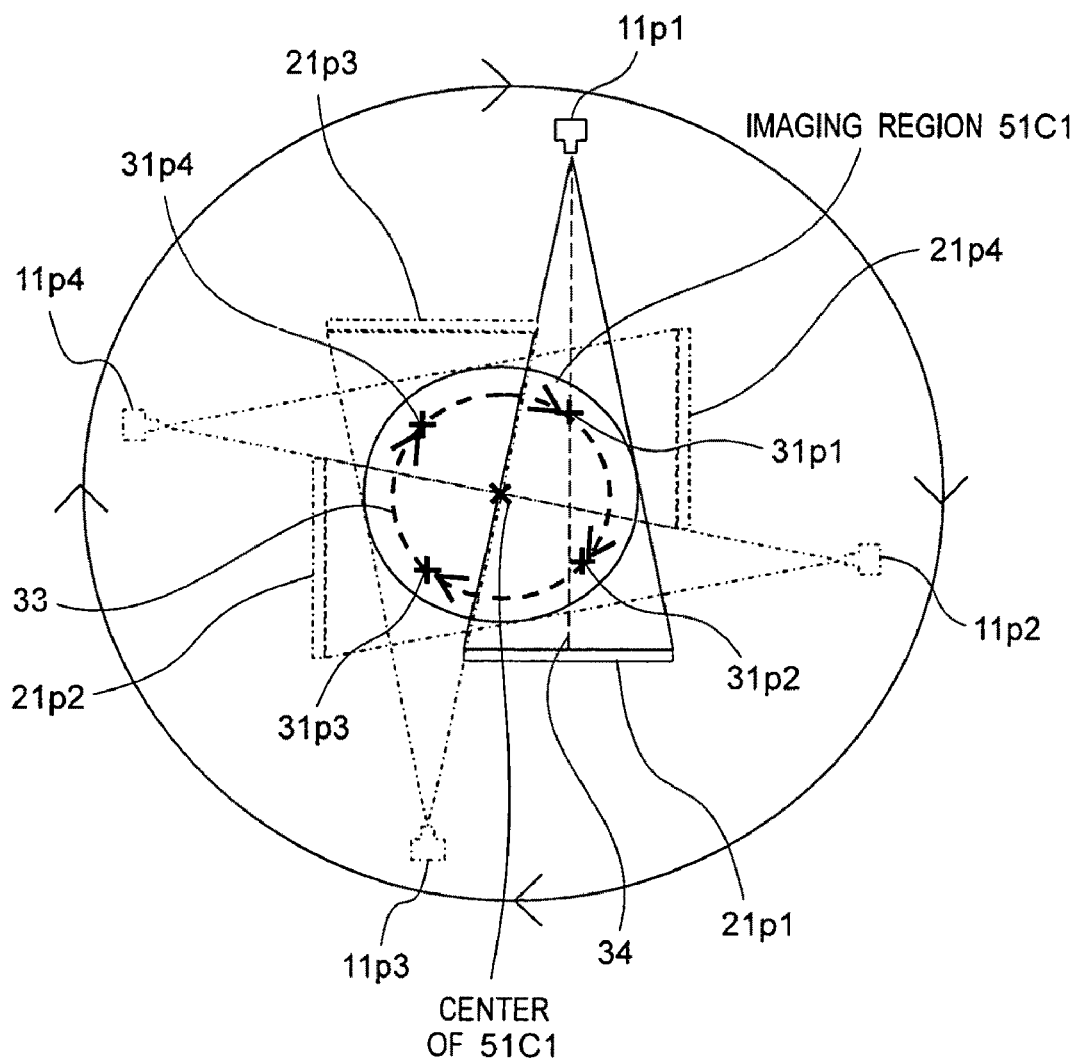
FIG. 2B is a diagram of another example of X-ray CT imaging with a magnifying factor larger than the counterpart used in FIG. 2A.

11: X-ray generator. 21: X-ray detector. 30: Rotary arm. (supporter). 31: Rotation center. 32 Rotary shaft. 40: Chair (Object holder). 51: Imaging region. 60: Controller. 60x: X-axis control motor. 60y: Y-axis control motor. 60z: Z-axis control motor. 60r: Rotation control motor. 61: Top frame (rotary shaft supporter). 41, 65: XY table (Movement mechanism).

Preferred Embodiments

Explanation of Reference Symbols

Embodiments the invention are explained below, referring to the appended drawings.

In CT imaging, an X-ray generator and an X-ray detector are circled around an object relative to the object. The X-ray generator exposes the object to an X-ray cone beam, and the X-ray detector having a two-dimensional detection plane detects X-rays transmitting the object. A larger object is desirable to be imaged in CT imaging. In the invention, in order to image a larger region, the center axis 34 of X-rays (or the symmetrical axis of an X-ray cone beam) does pass the center position (x) of the imaging region of an object and the center axis becomes tangent to an arc 33 having its center at the center position (x). Preferably, X-rays passing through the center of a region of interest of the object enter an edge of the two-dimensional detection plane of the X-ray detector. (A scan for imaging a larger imaging region with an X-ray cone beam by irradiating a part of the imaging region is referred to as offset scan.)

In the offset scan, a region imaged in each instant by the X-ray detector does not include the larger entire region to be imaged, but data necessary for image reconstruction on the entire region larger than the region imaged in each instant can be acquired. The imaging operation may be continued beyond 360 degrees. In order to enlarge an imaging region by setting a variable magnifying factor in CT imaging, the center (the rotary shaft) of the revolving motion of the X-ray generator and the X-ray detector is moved in two dimensions relative to the object to circle around the object.

The above-mentioned phrase of "relative to" means that various situations mentioned below are allowed. For example, the supporter supporting the X-ray generator and the X-ray detector is rotated, while the object is fixed, and the rotary shaft of the supporter is rotated. Alternatively, the supporter may be rotated, while the object is moved with a movement mechanism, and the position of the rotary shaft which supports the supporter supporting the X-ray generator and the X-ray detector is fixed. Alternatively, both the object and the supporter are moved. In the relative two-dimensional displacement of the rotary shaft, it is moved offset from the center of the imaging region in a plane crossing the rotary shaft along a circular orbit around the center of the imaging region. In CT imaging, a position relationship is required that the X-ray generator and the X-ray detector are revolved around an object while keeping the distances between the X-ray generator, the object and the X-ray detector constant. Therefore, in order to change the magnifying factor, the field of view in CT imaging has to be changed under the requirement on the position relationship. Such X-ray CT imaging is explained below.

For comparison, a normal X-ray CT imaging, without using offset scan is explained with reference to FIG. 1 on the positions of the X-ray generator, an object and the X-ray detector. (In the appended drawings, p1, p2, p3 and p4 added to the reference numerals represent four phases of successive rotation by 90 degrees.) An X-ray generator 11 and an X-ray detector 21 are attached to the two ends of a supporter (not shown), opposing to each other and interposing an imaging region 51A1 of an object between them. The X-ray generator 11 and the X-ray detector 21 are circled around the imaging region 51A1. The revolution center (+) of mechanical movement of the supporter supporting the X-ray generator 11 and the X-ray detector 21 coincides with the center position (x) of the imaging region 51A1 during a CT imaging process.

The center axis of an X-ray cone beam generated by the X-ray generator 11 passes the center x of the imaging region 51A1 and is detected by the X-ray detector 21. In the imaging, the X-ray generator 11 and the X-ray detector 21 are circled around the object in a certain direction. In the drawings, the positions of the X-ray generator 11 and the X-ray detector 21 are shown at four phases p1, p2, p3 and p4 in one circulation.

Next, various embodiments of offset scan X-ray CT imaging of the invention are explained.

Figure 3:
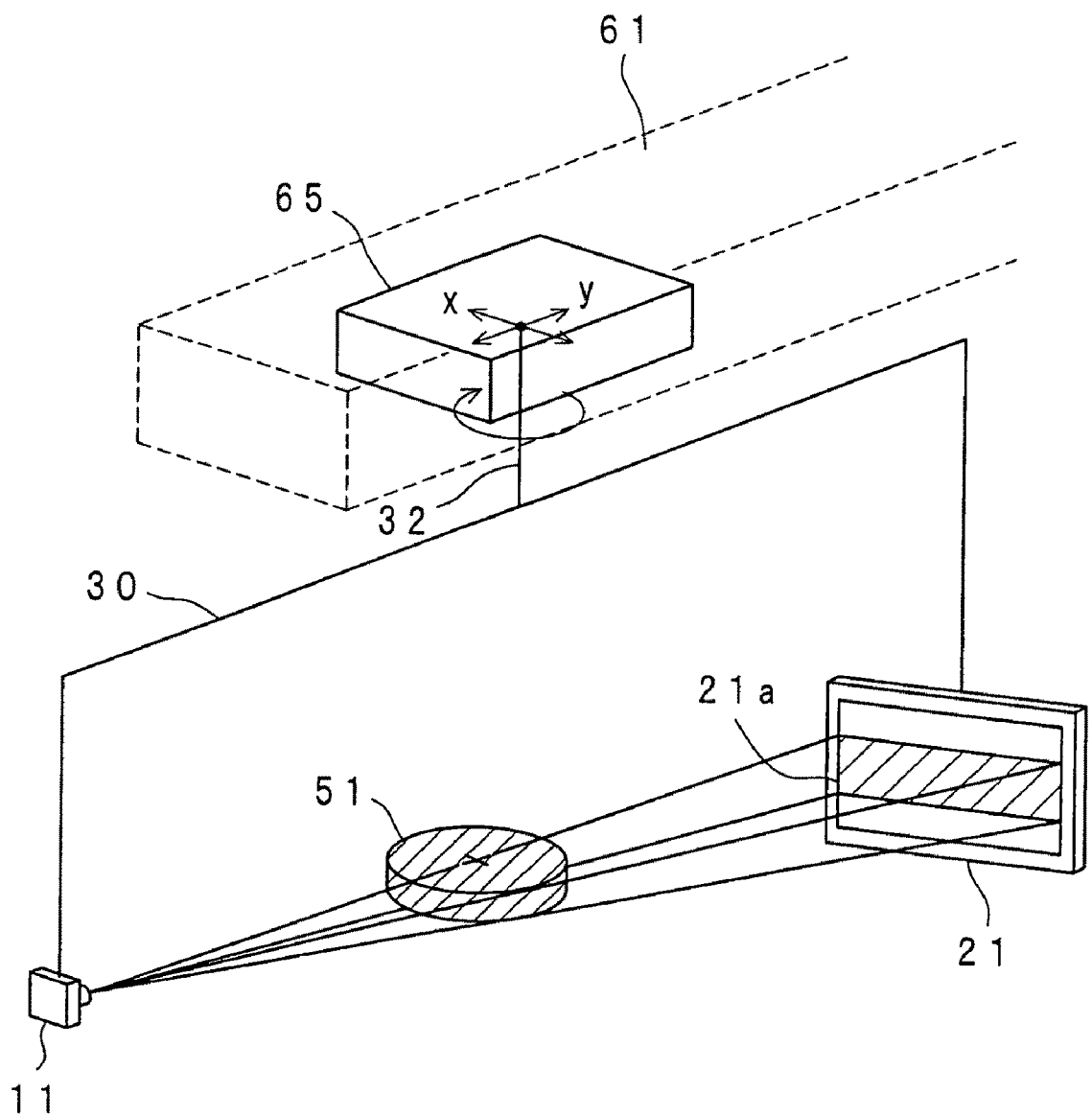
FIG. 3 is a diagram for explaining offset scan imaging.

FIGS. 2A and 2B schematically show the relative positions of the X-ray generator, an object and the X-ray detector in offset scan CT imaging in an embodiment of the invention at the four phases p1, p2, p3 and p4 of successive rotation by 90 degrees. The width of the imaging region becomes about twice and thrice in FIGS. 2 and 3 respectively, in contrast to that in the normal CT imaging shown in FIG. 1. The X-ray generator 11 generates an X-ray cone beam, and the X-ray detector 21 receives the X-ray cone beam transmitting the object.

In the offset scan imaging, the revolution center 31 (+) of the X-ray generator 11 and the X-ray detector 21 is offset relative to the center (x) of the imaging region 51B1, 51C of the object, and it is moved continuously as shown in the drawing with $31p1 \Rightarrow 31p2 \Rightarrow 31p3 \Rightarrow 31p4 \Rightarrow 31p1$. The center position (x) of the imaging region 51 is fixed at the center of a region of interest. The X-ray generator 11 and the X-ray detector 21 supported by the supporter so as to oppose to each other are circled around the object by a rotary shaft 32 (FIG. 3) supporting the supporter. Therefore, the revolution center 31 agrees with the position of the rotary shaft 32. The revolution center 31 (+) for the X-ray generator 11 and the X-ray detector 21 is separated from the center position (x) of the imaging region 51, and it is circled around the center position (x) of the imaging region. The circular trajectory of the revolution center 31 is shown with a dashed line.

The revolution period of the revolution center 31 agrees with that of the revolution of the X-ray generator 11 and the X-ray detector 21. A plane movement mechanism for moving the rotary shaft 32 or the revolution center 31 for the X-ray generator 11 and the X-ray detector 21 makes the revolution center 31 circle around the center position (x) of the imaging region 51 as shown in the drawings as $31p1 \Rightarrow 31p2 \Rightarrow 31p3 \Rightarrow 31p4 \Rightarrow 31p1$. The position of the rotary shaft 32 or the revolution center 31 is offset from the center position (x) of the imaging region in a plane crossing the rotary shaft 32. The trajectory of the circular motion is a true circle having a center thereof at the center (x) of the CT imaging region. The period of the circular motion agrees with the rotation of the supporter (rotary arm 30 in FIG. 3) by the rotary shaft 32. That is, in synchronization with one rotation of the supporter supporting the X-ray generator 11 and the X-ray detector 21 around the imaging region 51, the circular trajectory of the rotary shaft 31 revolves around the imaging region 51. Thus, the position of the X-ray generator 11 is moved as shown in the drawing with 11p1=>11p2=>11p3=>11p4=>11p1, while that of the X-ray detector 21 is moved as shown similarly in the drawing with 21p1=>21p2=>21p3=>21p4=>21p1.

When an image of the object is taken in the imaging plane of the X-ray detector 21, the magnifying factor is FS/FB wherein FS is distance between the X-ray generator 11 and the X-ray detector 21 and FB is distance between the X-ray generator and the center of the imaging region of the object. The magnifying factor can be changed by setting the distances FS, FB appropriately. Because the X-ray cone beam broadens as it propagates, the imaging region extends also in a direction vertical to the rotation plane. In the case of FIG. 2B, the magnifying factor becomes smaller by setting the center position (x) of the imaging region 51 nearer to the X-ray detector, relative to the case of FIG. 2A, and the imaging region becomes nearer to the X-ray detector and extends more in the horizontal and vertical directions.

In the offset scan imaging, X-rays along the symmetrical axis 34 of a broadening X-ray cone beam enter a position offset from the center (x) of the imaging region 5181, 51C1. In the examples shown in FIGS. 2A and 2B, the position of the X-ray generator 11 is offset, as shown schematically in FIG. 3, so that the X-rays passing the center of the imaging region 51 pass an edge 21a of the detection plane of the X-ray detector 21. In each instant, the X-ray cone beam irradiates a part (a half in the examples) of the imaging region 51, and the X-rays transmitting the part of the imaging region 51 strike on the x-ray detector 21. Thus, by a revolution by 360 degrees around the object, the entire imaging region is imaged, and a three-dimensional image of the object is reconstructed based on the projection data acquired above.

Next, the position relationship between the X-ray generator, the object and the X-ray detector is explained. The X-ray generator 11 and the X-ray detector 21 are rotated, while the rotary shaft 32 is moved in two dimensions by a movement mechanism such as an XY table 65. The supporter such as a rotary arm 30 for supporting the X-ray generator 11 and the X-ray detector 21 is supported by the rotary shaft 32, which is supported by the XY table 65. The XY table 65 includes a motor (not shown) for movement in X-axis and another motor (not shown) for movement in Y-axis. The movement mechanism shifts the X-ray generator 11 and the X-ray detector 21 by moving the rotary shaft 32 relative to the object 50. Further, while the supporter which supports the X-ray generator 11 and the X-ray detector 21 is shifted in a plane perpendicular to the rotary shaft 32, it is rotated by a motor (not shown) around the rotary shaft being displaced by the movement mechanism by driving the motors (not shown) incorporated in the XY table 65.

Then, the trajectory of the X-ray generator 11 and the X-ray detector 21 relative to the object 50 is obtained as a synthesized motion resulting from the simultaneous driving of the movement and revolution (first revolution) of the rotary shaft 32 around the object by a movement mechanism such as an XY table and the revolution (second revolution) of the X-ray generator 11 and the X-ray detector 21 around the rotary shaft 32 being displaced by the first revolution. The movement mechanism makes the first revolution synchronize with the second revolution. In concrete, the angular velocity of the second revolution is set to the same as the first revolution. Thus, the X-ray generator 11 and the X-ray detector 21 are revolved around the object 50 while the distance of the X-ray generator 11 and the X-ray detector 21 relative to the object is kept constant.

Situations of the relative rotation are shown schematically in FIGS. 4A and 4B as perspective views at the four phases p1, p2, p3 and p4 shown in FIGS. 2A and 2B. In the offset scan imaging, the object 50 is fixed at a predetermined position, and the rotary shaft 32 is rotated along a circular orbit by the plane movement mechanism such as the XY table 65 while the X-ray generator 11 and the X-ray detector 21 are revolved around the object 50 by the rotary shaft 32.

Figure 5B:
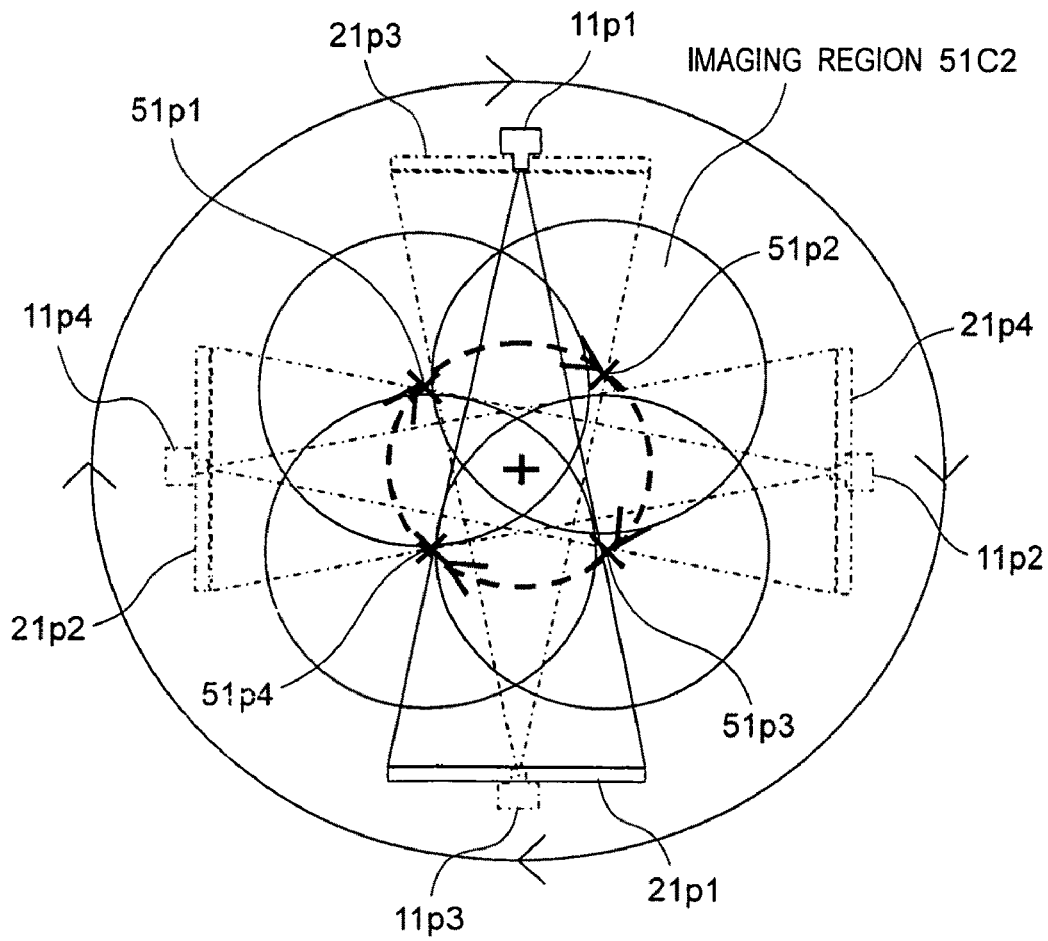
FIG. 5B is a diagram of another example X-ray imaging with a magnifying factor different from the counterpart used in FIG. 5A.

On the other hand, the X-ray generator and the X-ray detector are also moved or revolved around an object relative to the object even when the position of the rotary shaft is fixed and only rotation is allowed. FIGS. 5A and 5B show relative positions in such cases between the X-ray generator, the object and the X-ray detector at the four phases p1, p2, p3 and p4 in one revolution. In FIGS. 5A and 5B, the width of the imaging regions 51B2 and 51C2 is about double and twice as wide as that in the normal CT imaging shown in FIG. 1.

The revolution center (+) of the X-ray generator and the X-ray detector is set at a predetermined position, and the center position (x) of the imaging region 51 is offset from the revolution center (+) and is moved in a circle relative to the center position of the imaging region 51. The trajectory of the center of the imaging region 51 is shown with dashed lines. The symmetrical axis of the X-ray cone beam passes a position crossing the rotary shaft 32. The relative movement of the object can be performed, for example, by moving the object with the XY table 65 provided in a mechanism for holding the object while rotating the rotary shaft. This situation is shown in FIGS. 6A, 6B and 7 at the four phases p1, p2, p3 and p4 schematically. An object 50 is placed on a supporter 40, and the object 50 is moved by a movement mechanism such as a triaxial movement mechanism 41 provided in a chair for supporting the object or a plane movement mechanism 46.

Figure 8:
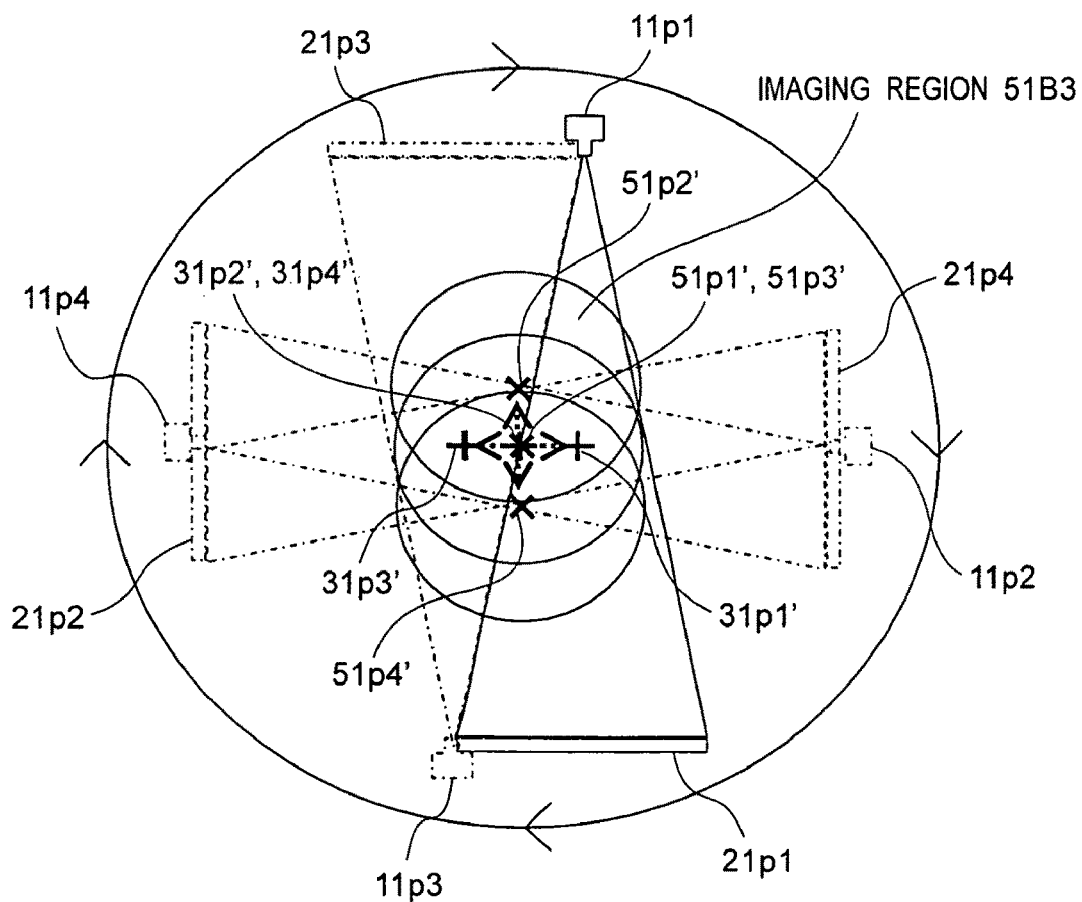
FIG. 8 is a diagram on the movement of the position of the rotary shaft in a different embodiment.
Figure 9:
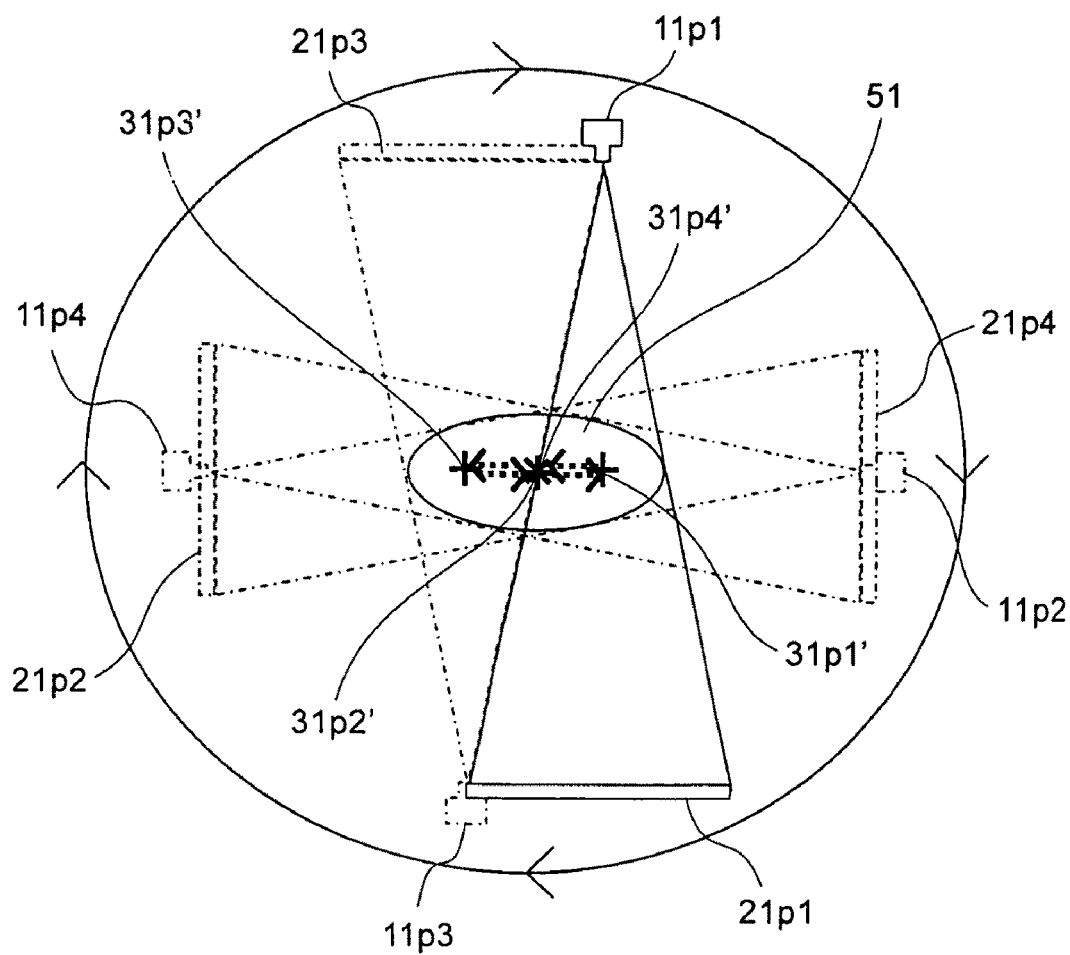
FIG. 9 is a diagram for explaining an embodiment for imaging an elliptical imaging region.
Figure 11:
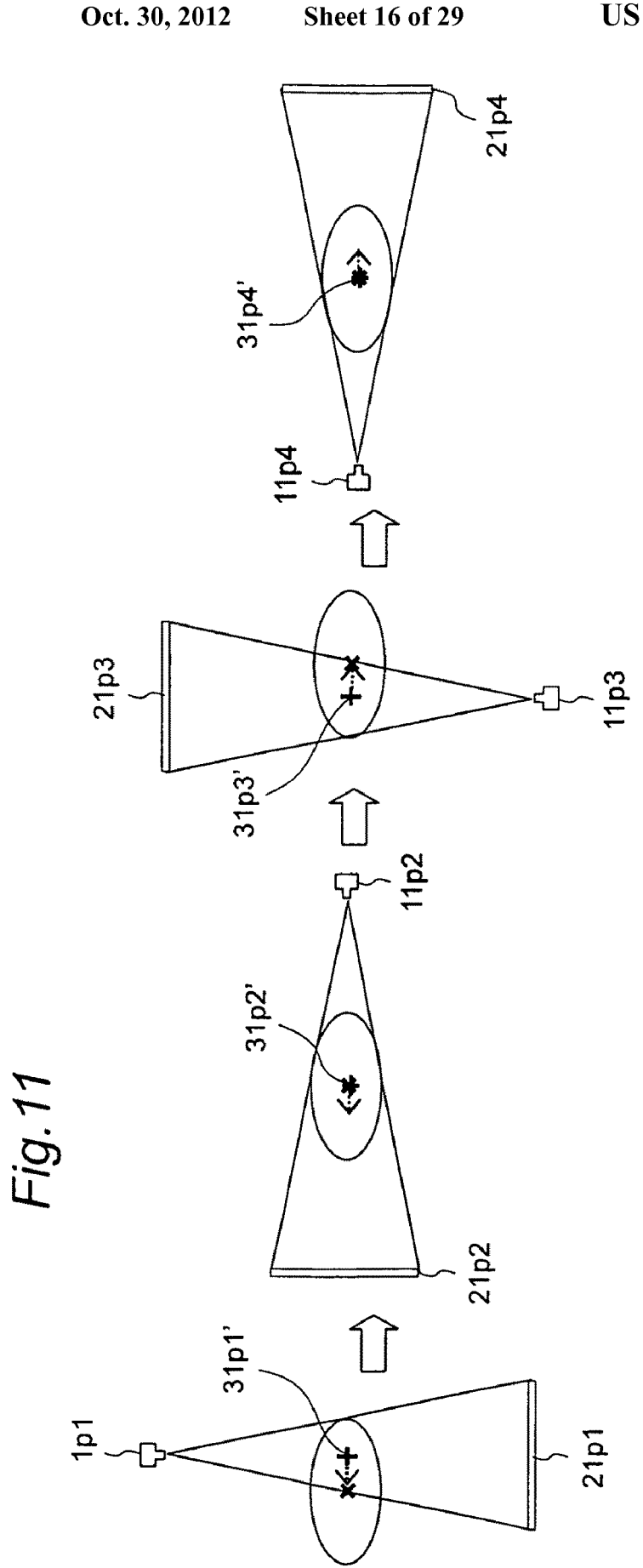
FIG. 11 is a sectional view at the four positions in the embodiment shown in FIG. 9.

Further, the above-mentioned movement of the revolution center can be combined with the movement of the center of the imaging region. For example, the revolution center of the X-ray generator and the X-ray detector is moved linearly in a first direction, and simultaneously the center of the imaging region 51 is moved linearly in a second direction crossing the first direction. In an example shown in FIG. 8, the relationship between the X-ray generator, the X-ray detector, the object and the rotary shaft is shown at the four phases p1, p2, p3 and p4. The rotary shaft 32 is moved linearly as shown in the drawing with 31p1'=>31p2'=>31p3'=>31p4'=>31p1', while the center (x) of the imaging region 51 is moved linearly as shown in the drawing with 51p1'=>51p2'=>51p3'=>51p4'=>51p1'. For example, by driving the X table in the supporting frame and the Y table in the object holder simultaneously, a synthesized motion is created wherein the revolution center is moved along a circular orbit relative to the object. Thus, the rotary shaft 32 is moved in a plane while it rotates. Alternatively, non-linear motions can be used instead of the linear motions.

The position of the rotary center 31 is not necessarily limited to that of the rotary shaft 32. For example, the rotary shaft 32 is revolved in the embodiments shown in FIGS. 4A and 4B, but the object may be revolved further. In medical cases wherein the object is a patient, it is desirable generally that the position of a patient is fixed and that the supporter is moved by a movement mechanism while revolved around the rotary shaft because a patient feels fear or bad when he or she is moved or revolved.

Next, an embodiment for imaging an elliptical region is explained. In an example shown in FIGS. 9, 10A, 10B and 11, a supporting frame 61 supports the rotary shaft 32 which rotatably supports the rotary arm 30 having the X-ray generator 11 and the X-ray detector 21. An X table 65c provided in the supporting frame 61 moves the rotary shaft 32 for the rotary arm 30 in X direction, while the position of the object 50 is fixed. Thus, an elliptical region 51 is imaged. Alternatively, the rotary shaft 32 can be moved linearly by the supporting frame in a direction, while the imaging region is revolved. Such an elliptical imaging region can be effectively used, particularly for a dental arch in dentistry. As mentioned above, the pattern of the trajectory of the rotary shaft 32 is not necessarily a circle, and an appropriate shape such as an ellipse can be adopted according to the purpose of the imaging.

Figure 12:
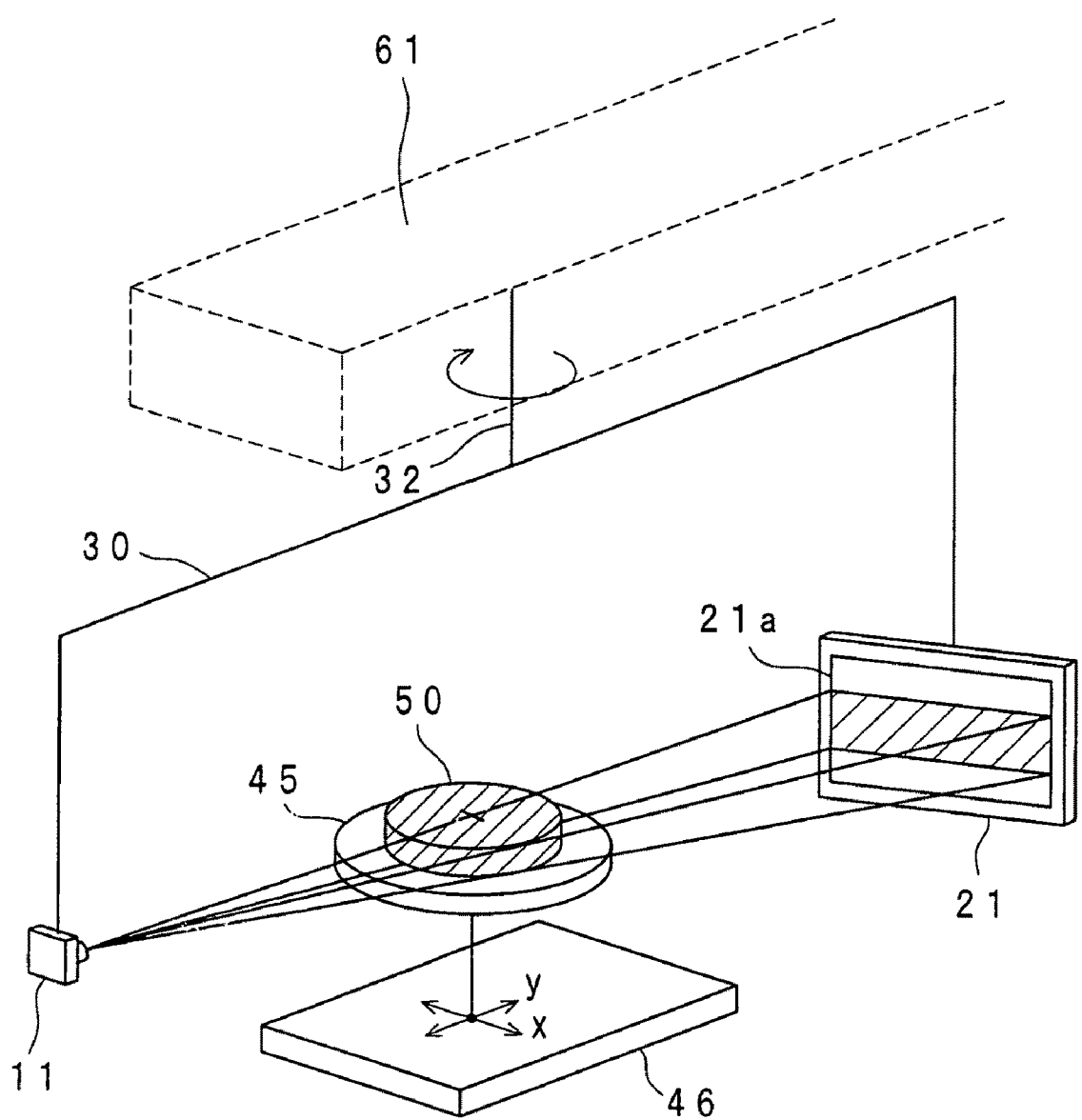
FIG. 12 is a diagram on an embodiment wherein an object is rotated.

Further, as shown in FIG. 12 schematically, an object 50 is placed on a table 45. The object 50 is rotated by rotating the table 45, while the positions of an X-ray generator 11 and an X-ray detector 21 are fixed. Such an apparatus can be applied for nondestructive testing to an object such as a semiconductor component other than a person. In this case, too, the X-ray generator 11 and the X-ray detector 21 are revolved relative to the object 50. A rotary arm 30 holds the X-ray generator 11 and the X-ray detector 21 at both ends thereof, while opposing them to each other. The X-rays passing the center of the imaging region of the object 50 strike the two-dimensional detection plane of the X-ray detector 21 at points offset from the center of the detection plane in the rotation direction. In this example, the X-ray passing the center of the imaging region of the object is arranged to strike an edge 21a of the two-dimensional detection plane of the X-ray detector 21.

A rotary shaft 32 for rotating the rotary arm 30 is supported rotatably by a supporting frame (shown with dashed lines), and the frame is fixed to a base (not shown). On the other hand, the object 50 is placed on the table 45, and a movement mechanism 46 moves the table 45 in the two-dimensional plane. The movement mechanism 46 is fixed to a base (not shown). Thus, the distances of the X-ray generator 11 and the X-ray detector 21 relative to the object 50 can be changed, and the magnifying factor can be changed. The movement mechanism 46 changes the position of the object 50 in a plane so as to revolve the object 50 around the rotary shaft 32. On the other hand, the rotary shaft 32 makes the X-ray generator 11 and the X-ray detector 21 revolve around the object 50 in a horizontal plane.

Therefore, the trajectory of the X-ray generator 11 and the X-ray detector 21 relative to the object 50 is obtained, if viewed from the object 50, as a result of synthesis of two motions driven simultaneously, that is, a revolution (first revolution) of the rotary shaft 32 around the object by the movement mechanism 46 such as an XY table, and a revolution (second revolution) of the X-ray generator 11 and the X-ray detector 21 around the rotary shaft 32 being displaced by the first revolution. The movement mechanism 46 synchronizes the first revolution with the second revolution. In concrete, the angular velocity of the first revolution is the same as that of the second revolution. Thus, the relative position relationship of the X-ray generator 11 and the X-ray detector 21 relative to the object 50 is kept constant, while the X-ray generator 11 and the X-ray detector 21 revolves around the object 50.

Next, the structure of the X-ray CT imaging apparatus is explained in detail.

Figure 13:
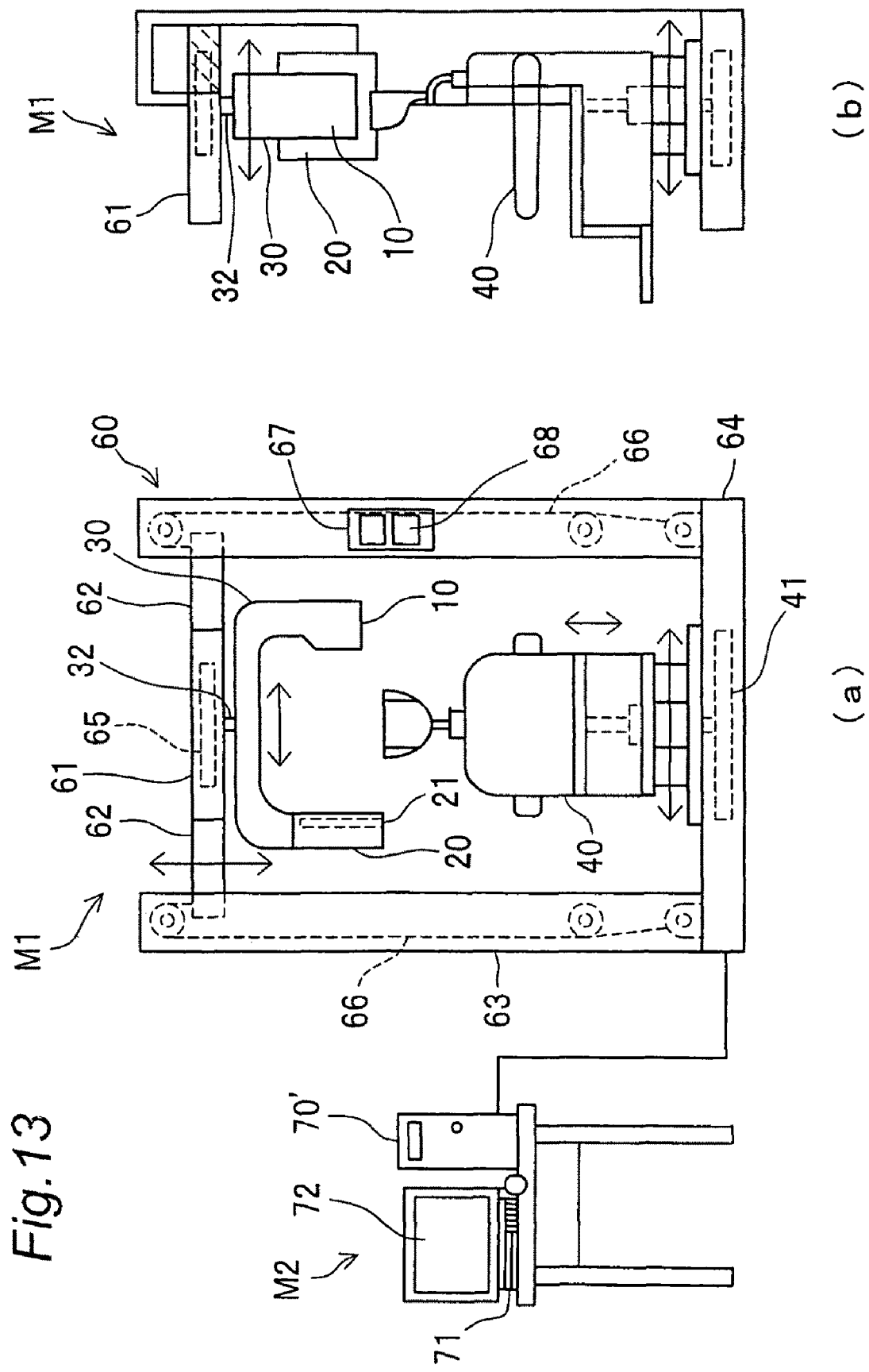
FIG. 13 is a front view and a side view of an embodiment of an X-ray CT imaging apparatus.

FIG. 13 shows (a) a front view and (b) a side view of a cone beam X-ray CT imaging apparatus according to an embodiment. The X-ray CT imaging apparatus has a main body M1 and a computer M2. In the main body M1, a main frame 60 having a very rigid structure has a top frame 61 (a device for rotatably supporting the rotary shaft) supporting a rotary arm (supporter) 30 at a lower side with a rotary shaft 32, a pair of lateral beams 62 fixing and holding the two ends of the top frame 61, a pair of vertical beams 63 supporting the lateral beams 61, and a base 64 fixing the pair of vertical beams 63. The base 64 is also a base of the entire apparatus.

An XY table (movement mechanism) 65 is provided inside the top frame 61, and the rotary shaft 32 for the rotary arm 30 is fixed to the XY table 65. The XY table 65 rotatably supports and displaces the rotary shaft 32. The rotary arm 30 is driven by a motor 60r (not shown) on imaging at a constant revolution speed around an object. The lateral beams 62 are moved up and down by a lift mechanism 66 provided in the vertical beam 63.

On the other hand, a triaxial movement mechanism 41 is provided on the base 63, and a chair 40 as a part of a device for holding an object is placed thereon. A device for fixing the patient's head is provided above the back of the chair 40. A triaxial movement mechanism is provided inside the chair 40, and an object sitting on the chair 40 is moved by the triaxial movement mechanism 41 in X, Y and Z directions or front and back, left and right, and up and down directions. X, Y and Z tables (not shown) for linear translation provided inside the triaxial movement mechanism 41 perform precise linear movement with a known cross roller guide, a conventional combinations of a bearing and a guide or the like.

The movement of the X, Y and Z tables for linear movement may have a mechanism such as a rack-and-pinion, a ball screw or a screwed shaft, and it is desirable that the position can be set precisely. The triaxial movement mechanism 41 is an example of a movement mechanism for moving an object in a plane perpendicular to the rotary shaft 32. In this embodiment, the triaxial movement mechanism 41 moves the chair 40 in a first direction such as X direction, in a second direction perpendicular to the first direction such as Y direction and in a third direction perpendicular to the first and second directions such as Z direction. However, the chair 40 is moved generally in a first direction and a second direction different from the first direction. In this example, a movement mechanism is provided both in the top frame and in the chair. Alternatively, it may be provided only in one of them. It is also possible that the movement mechanisms in the top frame and in the chair have different functions. For example, one of them has a mechanism for moving only in X direction and the other has a mechanism for moving only in Y direction.

An operational panel 67 used by an operator for instructing operations is provided at a surface of one of the vertical beams 63. The operational panel 67 has a display screen 68 for inputting and displaying instructions for various operations. The operational panel 67 also plays a role as a mode switch for changing between normal CT imaging mode and offset CT imaging mode. X-rays transmitting an object are detected as projection data by the X-ray detector 21, and the data is sent to the computer M2 having a main body 70', a keyboard 71 for receiving key-inputs and a display device 72.

Next, examples of the movement mechanism provided in the rotary arm 3 are explained. They can be applied to a gate type apparatus shown in FIG. 13 and to an apparatus shown in FIG. 17. A portion on the control of the position and rotation of the rotary arm (supporter) 30 is shown in a partially broken top view shown in FIG. 14 and in a partially broken top view shown in FIG. 15. Inside the top frame (rotary shaft supporter) 61, a movement mechanism is provided for displacing the position of the rotary shaft 32 for the rotary arm 30 in two dimensions. An XY table is used as the movement mechanism which can move front and back and left and right in two dimensions. The XY table has an X table 35X and a Y table 35Y. The Y table 35Y is moved by a motor 60y in the front-and-back direction (Y direction), and the X table 35X, supported by the Y table 35Y and supporting the rotary shaft 32 extending vertically, is moved by a motor 60x in a lateral direction (X direction) to move the rotary shaft 32. The motors 60x and 60y can be controlled independently of each other. The tables 35X, 35Y and the motors 60x, 60y are components of an example of the moving mechanism driven to move the rotary shaft 32 relative to the object 50 in two dimensions and to rotates the rotary shaft 32 to revolve the X-ray generator 11 and the X-ray detector 21 relative to the object at the same time.

Figure 15:
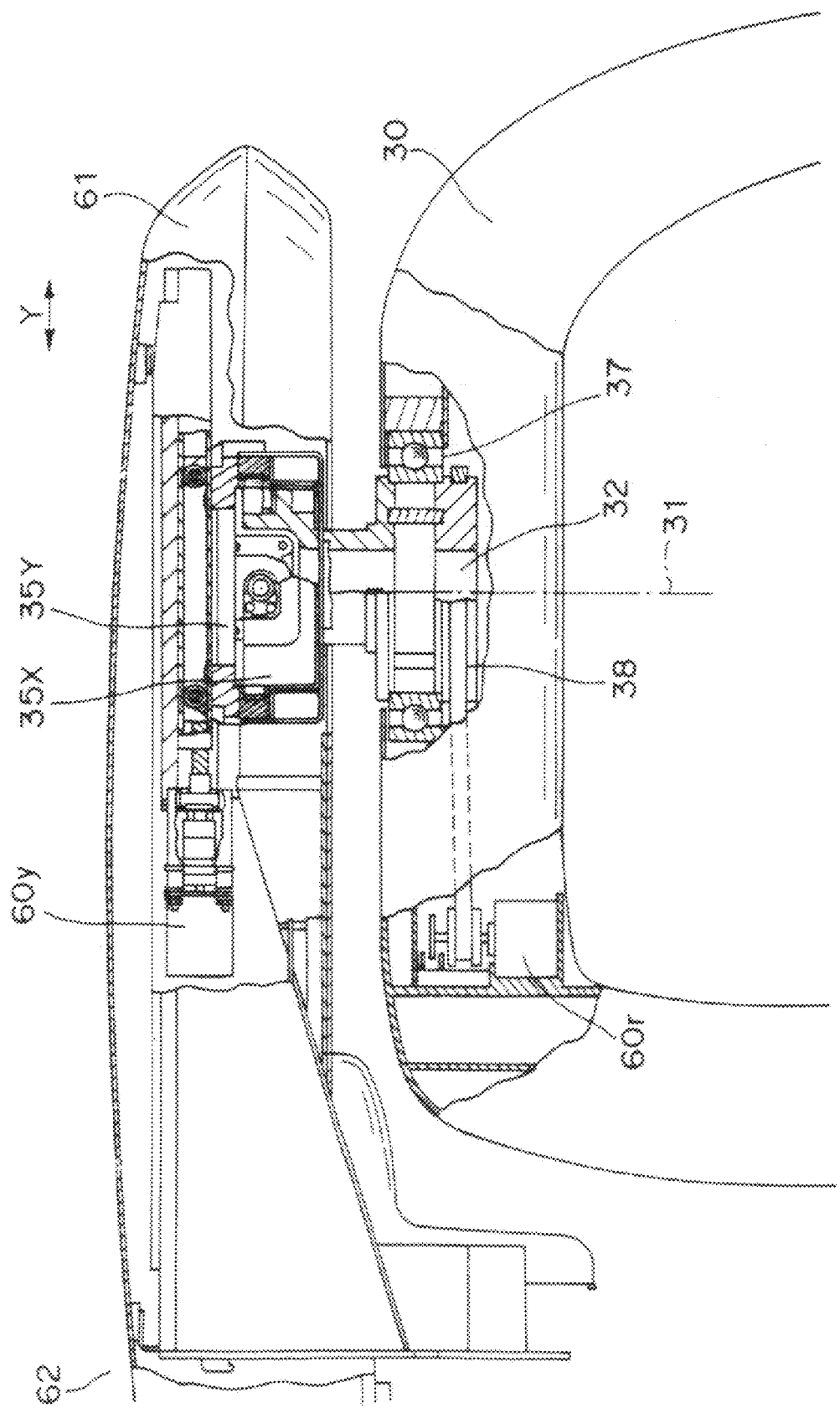
FIG. 15 is a partially broken side view of the plane movement mechanism.

The longitudinal direction of the rotary arm is denoted as Y direction, and a direction perpendicular to the Y direction is denoted as X direction in the position shown in FIG. 15. (Needless to say, two shafts movable in two dimensions can also be used, as will be explained later on FIG. 18 and the like.) The rotary shaft 32 is connected to a rotation table, which is connected to a rotary arm 30 via a bearing 37. A motor 60r transmits a rotation force with a belt 38 to the bearing 36 in order to rotate the rotary arm 30. The rotary shaft 32, the bearing 36, the belt 38 and the motor 60r are components of an example of a rotary mechanism for rotating the rotary arm 30. By driving a motor 60x for driving the X table 35X and another motor 60y for driving the Y table 35Y according to a predetermined program, the rotary shaft 32 can be moved front and back (Y direction) and right and left (X direction) while the rotary arm 30 is rotated.

Figure 14:
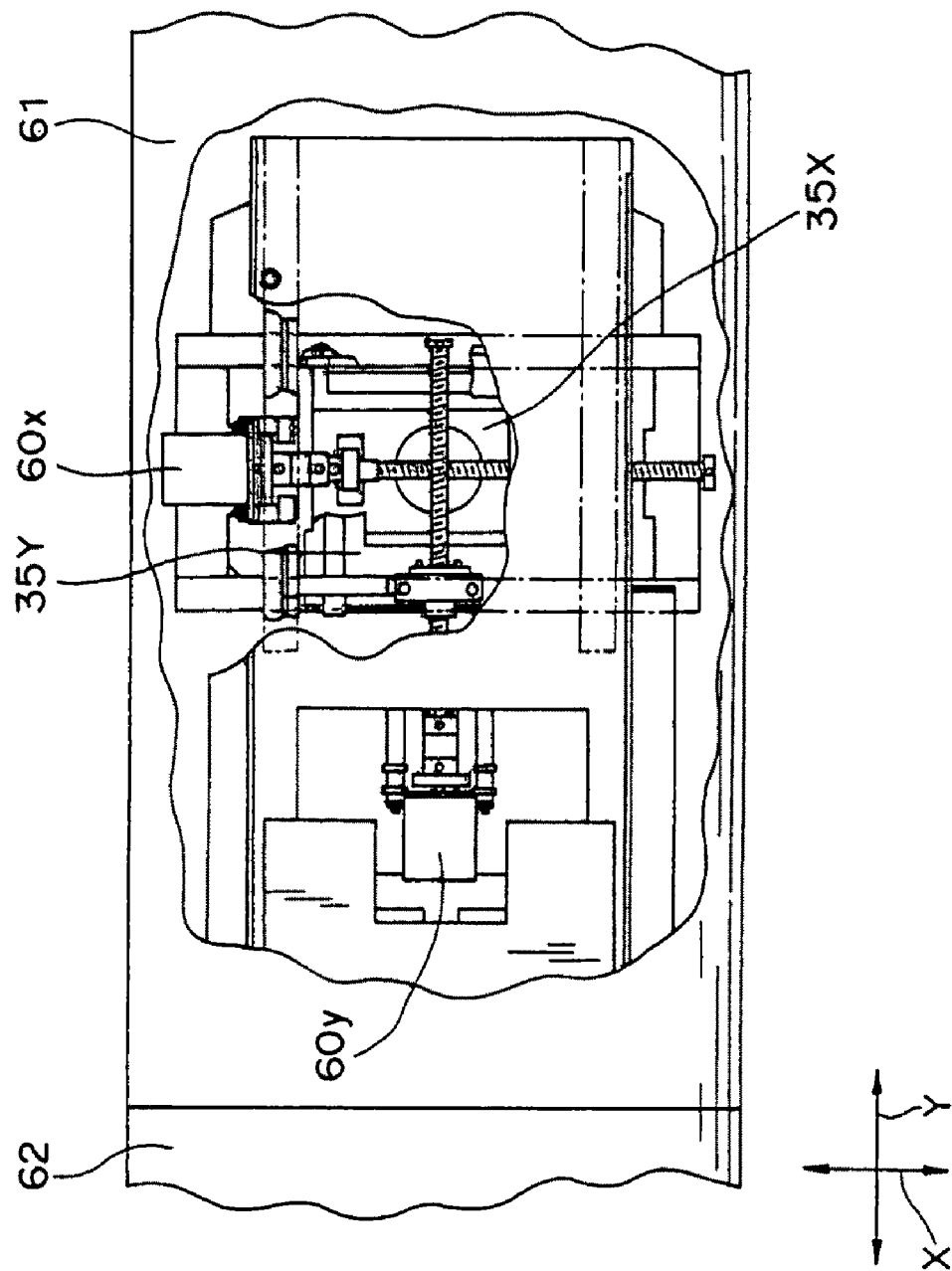
FIG. 14 is a partially broken top view of a plane movement mechanism.
Figure 16:
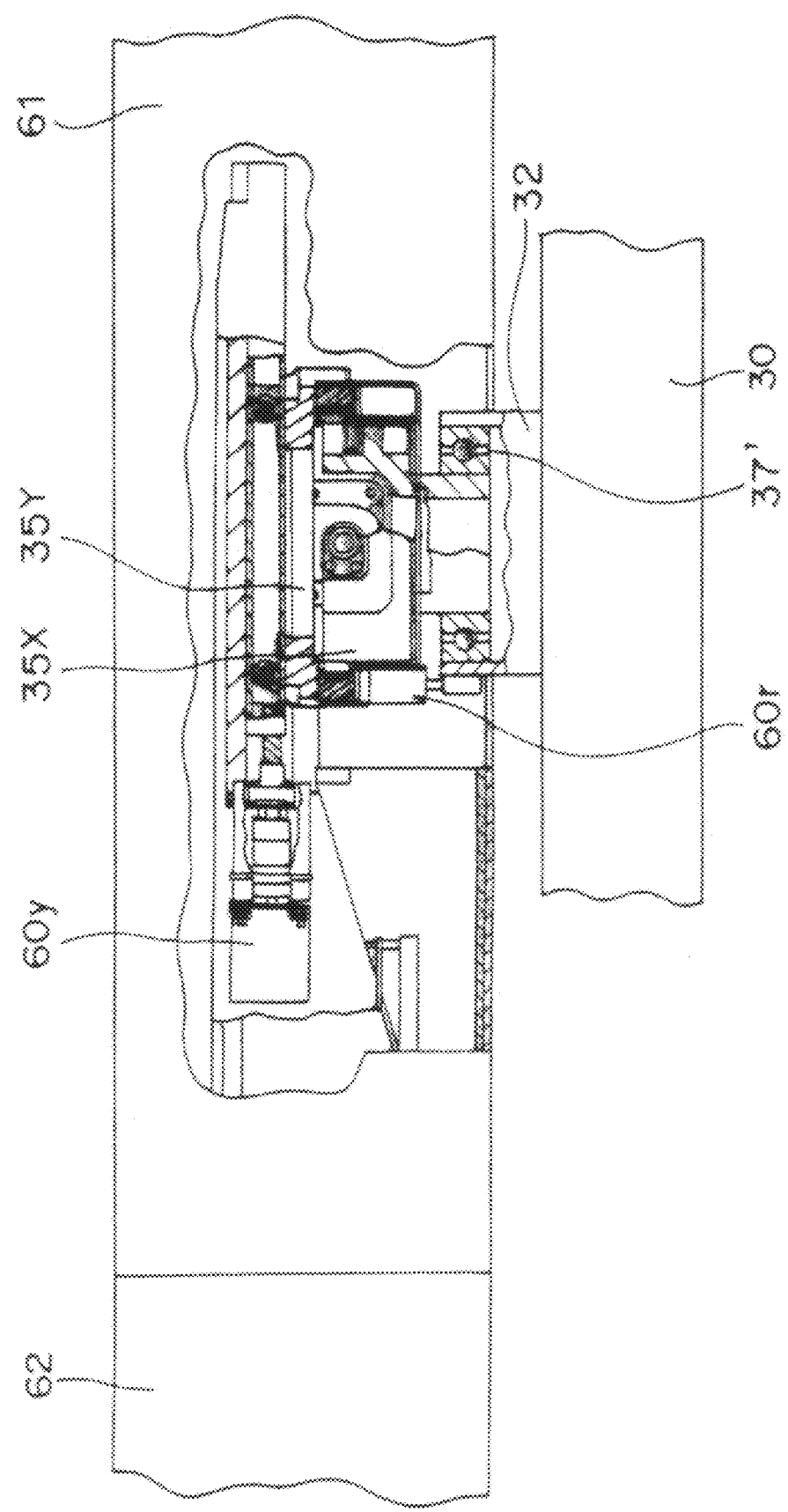
FIG. 16 is a partially broken top view of another example of a plane movement mechanism.

In the XY table shown in FIGS. 14 and 15, the motor 60r for controlling the rotation is provided at the side of the rotary arm 30. However, as shown in FIG. 16, X, Y tables 35X, 35Y and a motor 60r for controlling the rotation may be arranged in the same housing of the top frame 61. In the example shown in FIG. 16, the motor 60y for controlling Y axis drives the Y table 35y in Y direction in the housing of the top frame 61. The rotary shaft 32 for the rotary arm 30 is supported by the X table 35X supported by the Y table 35Y rotatably via a bearing 37'. The X table 35X is driven in X direction by a motor 60x for control in X axis. A belt for driving the bearing 37' is also arranged in the same housing though not shown in FIG. 16.

In the X-ray CT imaging apparatus shown in FIGS. 13 to 16, various types of CT imaging explained above with reference to FIGS. 2 to 16 can be performed. Needless to say, the structure of the X-ray CT imaging apparatus can be modified or simplified according to the type of CT imaging.

Figure 17:
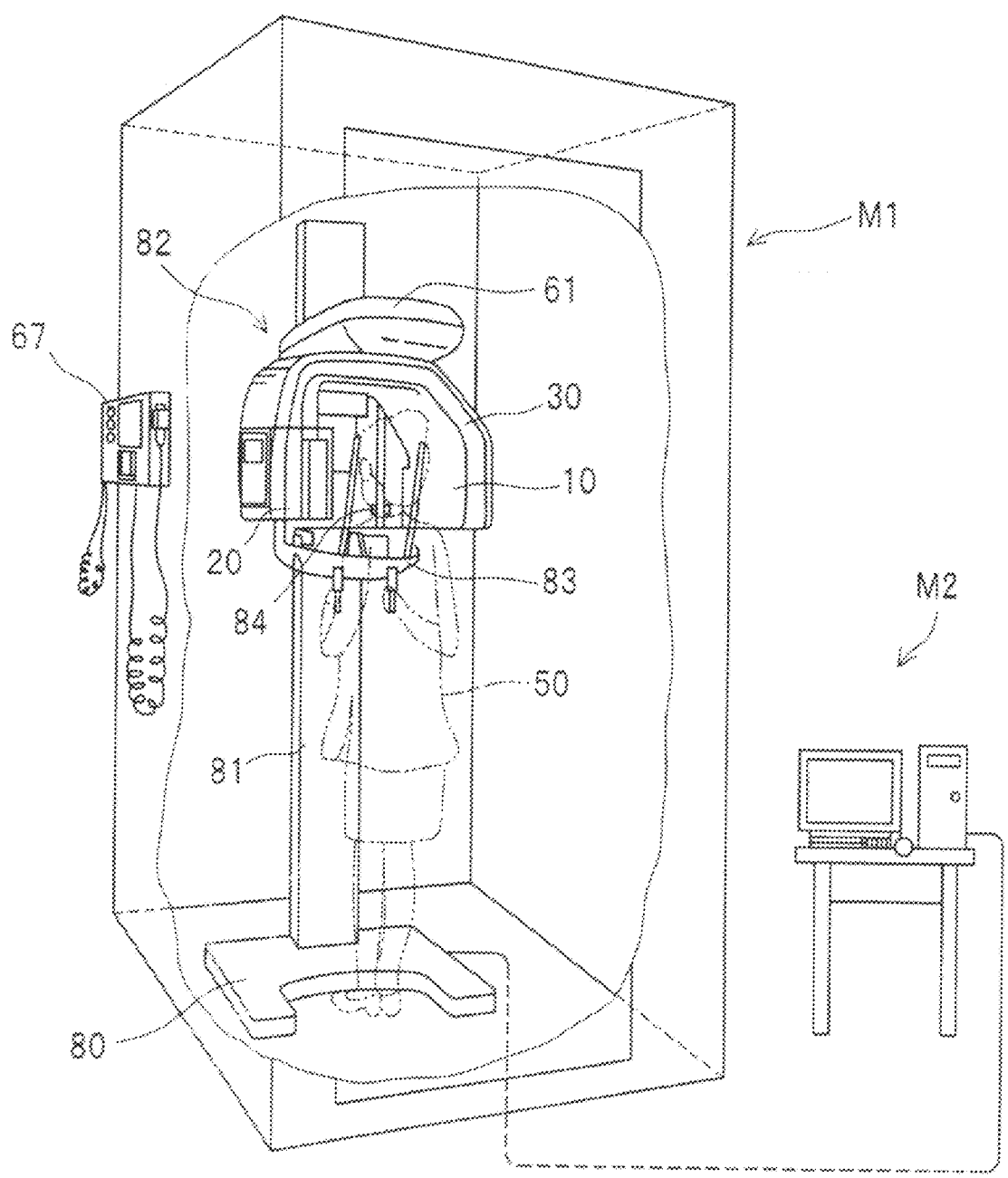
FIG. 17 is a diagram of a different embodiment of an X-ray CT imaging apparatus.

FIG. 17 shows another embodiment of the X-ray CT imaging apparatus. A main body M1 of the X-ray CT imaging apparatus has a base 80 placed on a base floor, an upright support 81 extending from the base 80, and a lift frame 82, while it does not include a chair. The lift frame 82 is attached to the upright support 81 so as to be moved up and down by a motor 60z (not shown) for controlling the up and down movement. The lift frame 82 has a bottom frame 83 extending horizontally from the lower end thereof, and the bottom frame 83 has a chin rest 84 so that the position of a patient can be adjusted easily. A patient as an object 50 stands before the base 80 and places his or her chin on the chin rest 84. The patient's head is interposed and immobilized by side holders (not shown) extending from the two sides of the chin rest 84. Thus, the object is positioned so that a region of interest to be imaged is located at an imaging region. Further, a top frame 60 extends forward from a top end of the lift frame 82, and it supports the rotary arm 30 rotatably.

The rotary arm (supporter) 30 has a U-character shape, and it has an X-ray generation section 10 and an X-ray detection section 20, opposing to each other. A plane movement mechanism as shown in FIGS. 14 and 15 is arranged inside the top frame 61, but the explanation on the plane movement mechanism is omitted here for the brevity of explanation. In CT imaging, the rotary arm 30 is rotated, and the object 50 is exposed to an X-ray cone beam, while X-rays transmitting the object are detected by the X-ray detection section 20 as projection data. The detected projection data is sent to a computer M2, similarly to the X-ray CT imaging apparatus shown in FIG. 13, but the detailed explanation is omitted here. In the X-ray CT imaging apparatus, an X-ray CT imaging which does not need to move an object is possible among various embodiments of CT imaging explained with reference to FIGS. 2 to 11.

In order to move the rotary shaft, a different rotary shaft movement mechanism can be used instead of the above-mentioned bearing or XY table. For example, a connection member or a plurality of connection members connected in series may be used to move the rotary shaft in a plane perpendicular to the rotary shaft. For example, the connection member is a member which can be extended freely.

FIG. 18 shows another example of a plane movement mechanism controlled with polar coordinates schematically. The plane movement mechanism has two arms AM1 and AM2. A reference point PT1 is fixed relative to the main body of the X-ray imaging apparatus, and a first arm AM1 is supported at the point PT1 rotatably. Further, the other end of the first arm AM1 is connected rotatably to en end of the second arm AM2, and the other end of the second arm supports the rotary shaft (+) of the rotary arm rotatably.

The two arms AM1, AM2 and the rotary shaft 32 are controlled by motors (not shown) provided for controlling the rotation angles. The rotation angle θ1 of the first arm AM1 relative to the main body of the X-ray imaging apparatus and the relative rotation angle θ2 of the second arm AM2 relative to the first arm AM1 are controlled by the motors for controlling the rotation angles so as to move the rotary shaft 32 in the two dimensional plane perpendicular to the rotary shaft. In the upper side in FIG. 18, the positions of the X-ray generator 11, the rotary shaft (+) and the X-ray detector 21 are shown at the four phases of successive rotation by 90 degrees as shown with arrows.

As explained above, the first part for moving the position of the rotary shaft in a first direction in the plane perpendicular to the rotary shaft may be an X table 35x in an XY table or a first arm AM1 in a plane movement mechanism controlled with the polar coordinates. Further, the second part for moving the position of the rotary shaft in a second direction different from the first direction may be a Y table 35Y in the XY table or a second arm AM2 in the plane movement mechanism. The rotary shaft held at the end of the second arm AM2 is moved easily by the rotations by the motors.

Further, when the irradiation field of X-ray beam is limited to create an X-ray narrow beam, at least one of panorama X-ray imaging and cephalometric imaging can be performed. For example, a dual-purpose apparatus can be realized by adding a panorama imaging function to an X-ray CT imaging apparatus by making it possible for panorama imaging to create a narrow beam and to limit an area in a sensor from which data are read. For example, as shown in FIG. 19, a primary slit mechanism 12 is arranged near the X-ray generator 11 at the front side thereof. It can set a plurality of slit openings (irradiation fields) for applications such as CT imaging, panorama imaging and the like.

The primary slit mechanism 12 is an example of a device for limiting an irradiation field for limiting an X-ray beam generated by the X-ray generator to an X-ray narrow beam extending in a direction in parallel to axial direction of the rotary shaft. Alternatively, a mechanism made of a pair of shielding members for controlling the width of an opening and another pair of shielding members for controlling the height of the opening is provided. The slit opening is adjusted by moving each of the shielding members in the two pairs by motors to set the distances between the pairs of the shielding members, as desired, in correspondence to the width and the height of the slit opening. FIG. 19 shows a case (a) of CT X-ray imaging and a case (b) of panorama X-ray imaging. For CT imaging, the primary slit mechanism 12 is activated by a motor (not shown) so that a rectangular slit opening for CT imaging is moved before the X-ray generator 11. For panorama imaging, the primary slit mechanism 12 is activated so that an opening with a narrow slit is moved before the X-ray generator 11.

Figure 20:
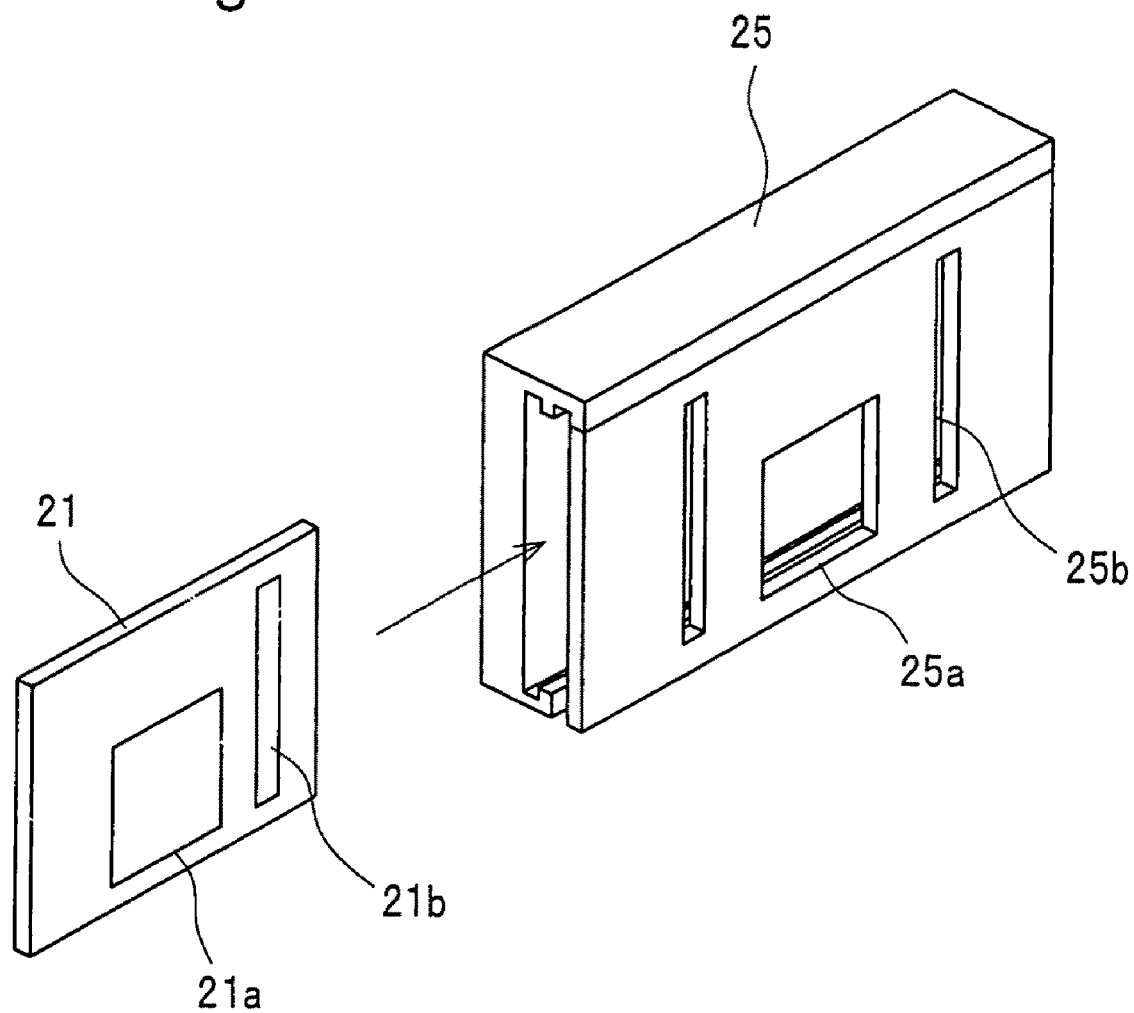
FIG. 20 is a diagram of an example of the X-ray detector.

In the X-ray detection section 20, a second slit mechanism may be arranged before the X-ray detector 21 in order to limit the irradiation field to the X-ray detector 21. In an example shown in FIG. 20, an X-ray detector 21 having an X-ray sensor 21a for CT imaging and an X-ray sensor 21b for panorama imaging can be inserted in a cassette 25. The cassette 25 as a secondary slit mechanism has a slit opening 25a for CT imaging and another slit opening 25b for panorama imaging. When the type of imaging is selected, the slit opening in correspondence to the selected type is positioned before the relevant X-ray sensor used for the selected type in the X-ray detector 21.

In panorama imaging, the X-ray generator 11 has to project a narrow beam along the dental arch generally in frontward direction. Then, when panorama imaging is instructed, a control section 70 sets a narrow irradiation field such as 10 mm times 60 mm to generate a narrow beam and limits an area from which data is read in the two-dimensional dental X-ray detector 21. Then, the XY table 65 is controlled while the rotary arm 30 is rotated by the rotary shaft 32, so as to move the X-ray generator 11 and the X-ray detector 21 in correspondence to the trajectory for panorama imaging. Thus, the rotary shaft 32 is rotated, while the revolution center is moved continuously along the trajectory of panorama imaging for projecting the narrow beam in the frontward direction in the course of rotation. Then, a panorama image is reconstructed by placing image data side by side in lateral direction in the sequence of imaging operation.

Next, control systems for the X-ray CT imaging apparatuses are explained.

Figure 21A:
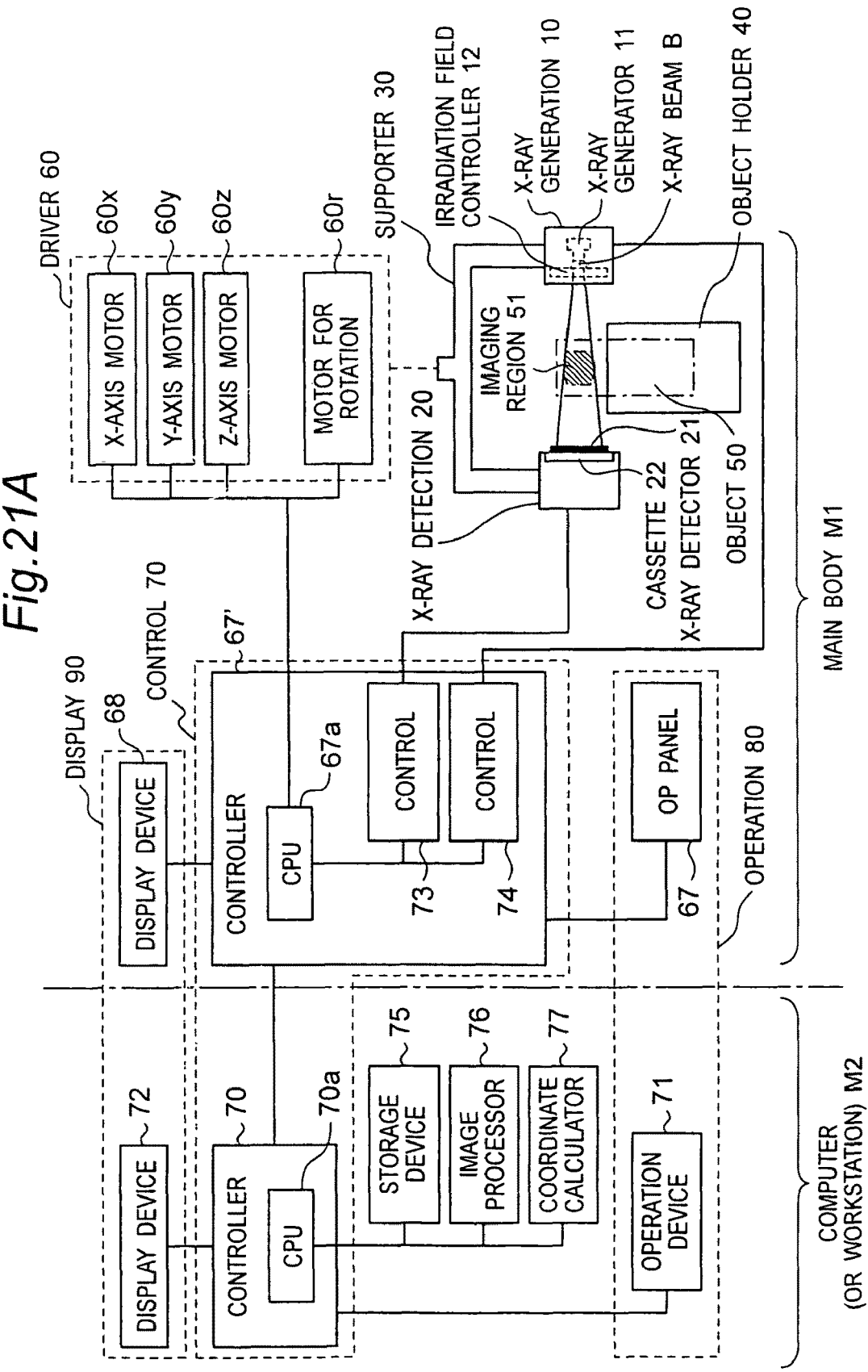
FIG. 21A is a diagram of a control system of an X-ray imaging apparatus.

A control system for an X-ray CT imaging apparatus shown in FIG. 21A is applied to an X-ray CT imaging apparatus wherein an object is fixed while CT imaging is performed, The X-ray CT imaging apparatus has a main body M1 and a computer (or a workstation) M2. An X-ray generator 11 in an X-ray generation section 10 for generating an X-ray cone beam and a two-dimensional X-ray detector 21 in a cassette 22 in an X-ray detection section 20 are supported at two ends of a supporter (such as a rotary arm 30) while opposing to each other, and they are rotated around an object 50 held by an object holder 40. The position of the X-ray detector 21 is shifted so that the X-ray beam does not pass the center of an imaging region 51 of the object 50, while the revolution center 32 is moved along a circle 33 around the center position (x) of the imaging region of the object. Thus a wider region can be imaged.

As shown in FIG. 16, the top frame supporting the supporter 30 includes the motor 60x and the motor 60y for moving along X-axis and along Y axis, respectively, and the motor 60r for rotation, and the motor 60z for lifting the top frame along Z-axis. The X-axis motor 60x, the Y-axis motor 60y and the Z-axis motor 60z move the XY table for supporting the rotary shaft in X, Y and Z directions. Further, the motor 60r provided for rotation rotates the supporter 30 via the rotary shaft.

A controller 67' provided in the main body M1 of X-ray imaging apparatus has a central processing unit (CPU) 67a for controlling the entire main body, and the CPU 67a controls the X-ray generation section 10 and the X-ray detection section 20 with control devices 73 and 74 controlling the X-ray generation section and the X-ray detection section respectively. The controller 67' is further connected to an operation device 67 to be operated by an operator for inputting an instruction and a display device 68 for displaying information to the operator.

Further, the controller 70' in the computer M2 has a central processing unit (CPU) 70a for controlling the entire computer, and the CPU 70a is connected to a storage device 75a, an image processor 76 and a coordinate calculator 77. The controller 70' is further connected to an operation device 71 to be operated by an operator for inputting an instruction and a display device 72 for displaying information to the operator.

In CT imaging, if a magnifying factor is set with the operation panel 67 before starting CT imaging, the controller 67' activates the motors 60x and 60y for moving in the X-axis and in the Y-axis so as to move the object relative to the X-ray detector 21 towards the X-ray detector 21 and vise versa. Further, the motor 60z for moving in the Z-axis is activated to adjust the height of the X-ray generator 11 and the X-ray detector 21 relative to the object 50. When CT imaging is started, the controller 67' activates the motor 60r to rotate the rotary arm (supporter) 30 and controls the motors 60x and 60y to move the revolution center along a circle having a predetermined radius. The principle of the imaging has already been explained with reference to FIG. 2 and the like.

The storage device 75 in the controller 70' stores a control program for controlling CT imaging and a calculation program for calculating three-dimensional CT data from the projection data. With the operation panel 67, an operator sets the type of imaging (for example, CT imaging or panorama imaging), irradiation field and the like. Based on the operator's instructions received from the operation panel 67, the controller 67' in the main body M1 controls the X-ray imaging apparatus by activating the programs for various controls and data processing. The controller 67' moves the rotary shaft 32 for the rotary arm 30 in X and Y directions by controlling the motors 60x and 60y and moves up and down the rotary arm 30 by activating the motor 60z.

The controller 67' controls the primary slit mechanism 12 at the side of the X-ray generator 11 and the secondary slit mechanism 25 at the side of the X-ray detector 21 so as to change the irradiation fields for the X-ray generator 11 and the X-ray detector 21. Further, the controller 73 controls the X-ray detector 21 to read X-ray image data. On imaging, the rotary shaft 32 is revolved around the object with the XY table and at the same time the motor 60r is driven at a constant speed to rotate the rotary shaft 32 so as to rotate the rotary arm 30 around the object. Thus, an X-ray cone beam is irradiated to the object 50 and the X-ray transmitting the object is detected by the X-ray detector 21, while the X-ray generator 11 and the X-ray detector 21 are revolved, and the X-ray image data acquired with the X-ray detector 21 are stored in the storage device 75.

The image reconstruction program in the image processor 76 reconstructs an image with the coordinate calculator 77 based on the X-ray image data at the pixels acquired in the storage device 75. The reconstruction calculation may be performed similarly to the case of half-scan disclosed in JP-A 2002-204796. It is different from a calculation for a normal CT imaging, for example, on a horizontal table on correspondence between a pixel in the two dimensional detection plane of the X-ray detector 21 and a voxel in the imaging region. It may be prepared only on a part of the imaging region.

Figure 21B:
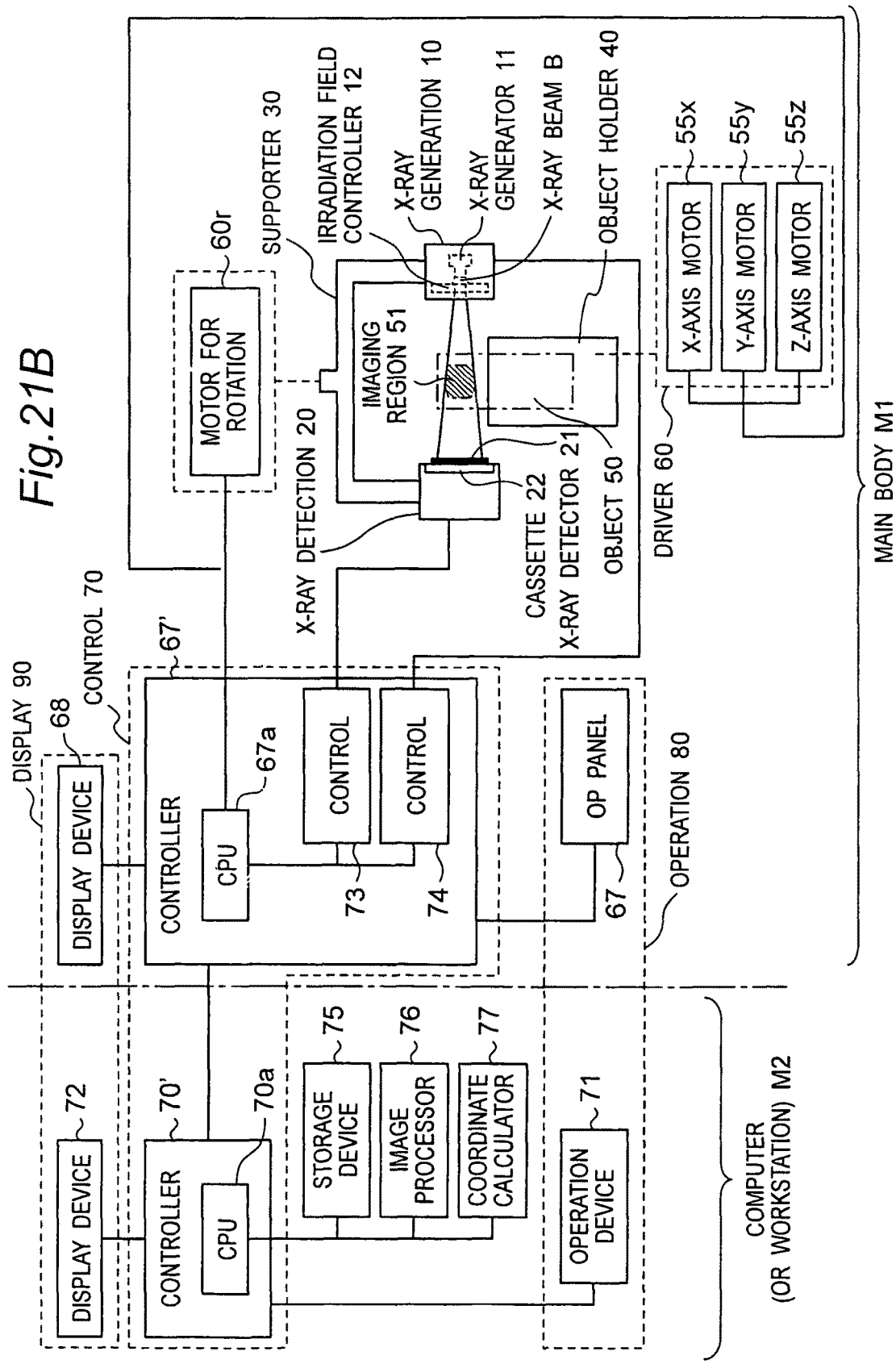
FIG. 21B is a diagram of another example of a control system of an X-ray imaging apparatus.

A control system for an X-ray CT imaging apparatus shown in FIG. 21B is applied to a XT imaging apparatus wherein an object is moved. It is different from the control system shown in FIG. 21A in a point that a driver section 55 for the triaxial movement mechanism is provided for driving the object holder 40. In the driver section 55, the X-axis motor 55*x*, the Y-axis motor 55*y* and the Z-axis motor 55*z* are driven. The motor 60*r* for rotating the supporter 30 is provided in the supporting frame, similarly to the control system shown in FIG. 21A. Except the above point, the control system shown in FIG. 21B is similar to that shown in FIG. 21A, and detailed explanation is omitted here.

Figure 21C:
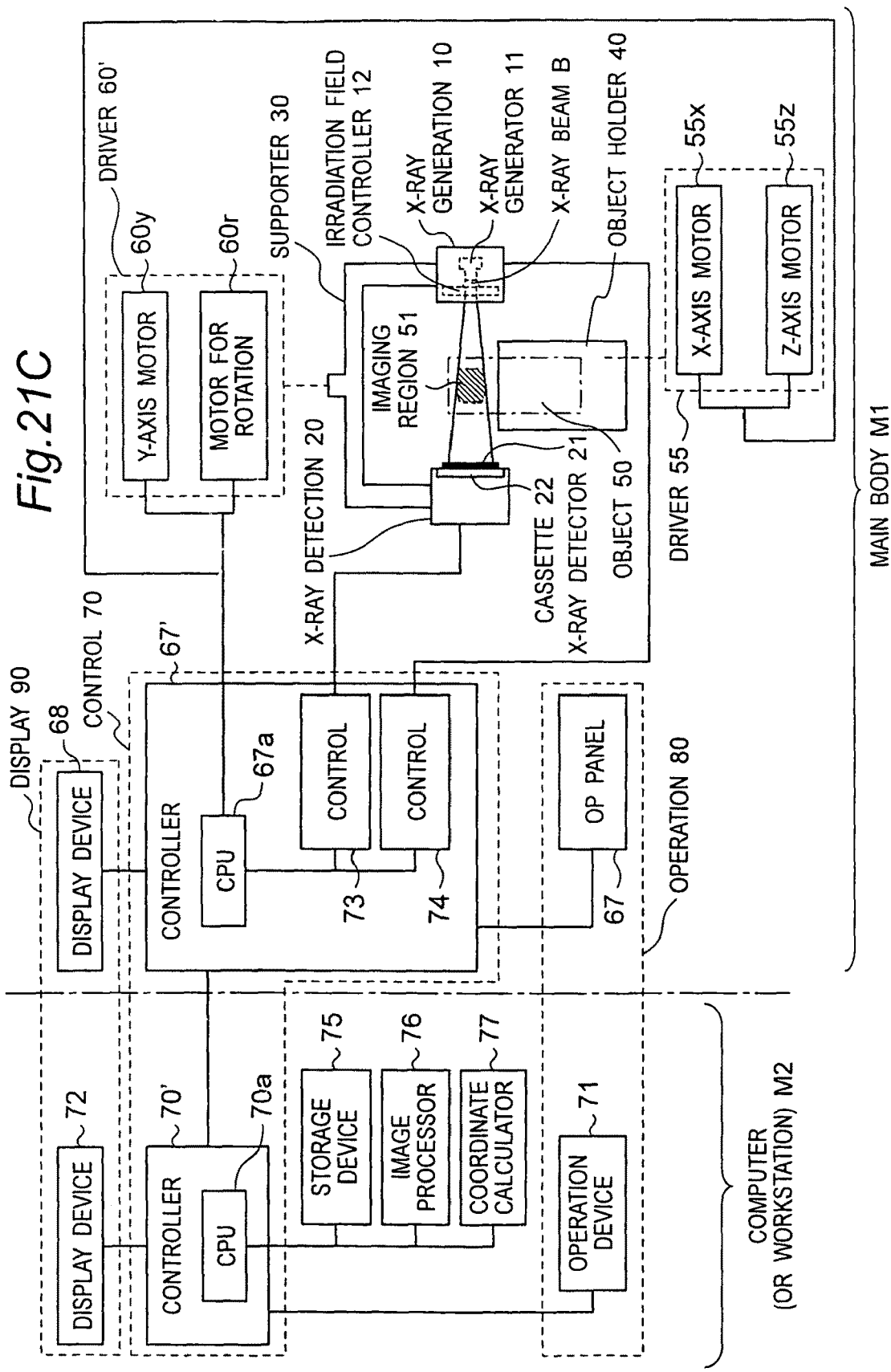
FIG. 21C is a diagram of a further example of a control system of an X-ray imaging apparatus.

A control system for an X-ray CT imaging apparatus shown in FIG. 21C is used for a CT imaging apparatus wherein an object is moved while the rotary shaft is also moved in CT imaging. In contrast to the control system for an X-ray CT imaging apparatus shown in FIG. 21A, the Y-axis motor 60*y* for the Y table is provided besides the motor 60*r* for rotation, while an XZ table is provided in the side of the object holder 40 including the X-axis motor 60*x* for driving the X table and the Z-axis motor 60*z* for driving the Z table. Except the above points, the control system is similar to that shown in FIG. 21A, and detailed explanation is omitted here.

Figure 22:
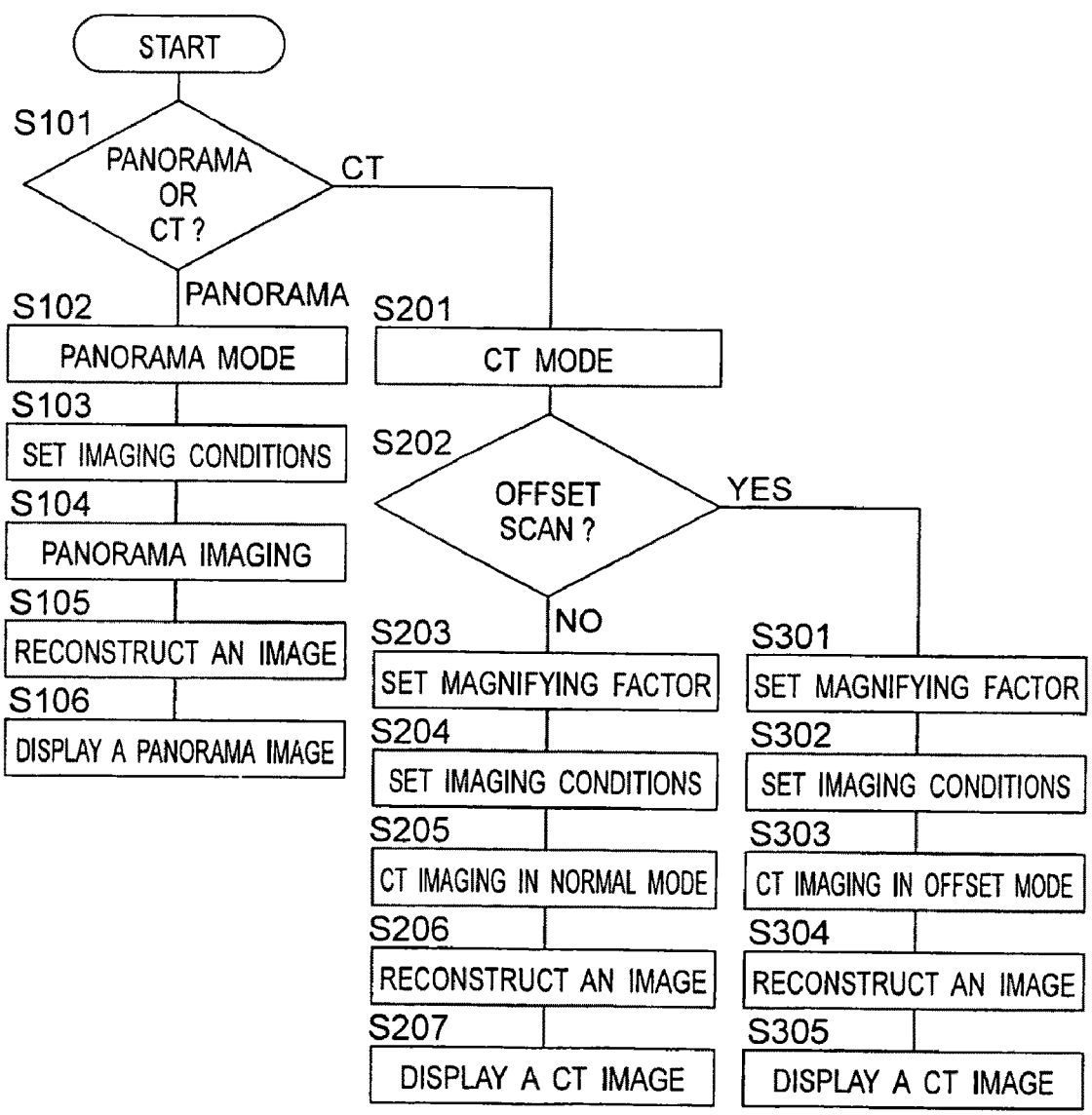
FIG. 22 is a flowchart for controlling revolution.

FIG. 22 shows a flowchart of imaging control by the CPU 67*a* in the controller 67' in the double-purpose apparatus for CT and panorama imaging for controlling imaging operations. First, it is decided whether the imaging type instructed by an operator is panorama imaging or CT imaging. (S101). If the imaging type is panorama imaging, panorama mode is set to the apparatus (S102), and imaging conditions for panorama imaging are set to the apparatus (S103). For example, a slit for panorama imaging is selected, an X-ray beam orbit for panorama imaging is selected, the object and the rotary arm are positioned relative to each other, parameters for the rotation of the rotary arm 30 and the movement of the rotary shaft 32 are set, and a range from which data is read is set to the X-ray detector 21. Then, panorama imaging is performed with the imaging conditions mentioned above (S104). Next, a panorama image is reconstructed (S105), and the obtained panorama image is displayed (S106). In the case of the CT imaging apparatus which does not perform panorama imaging, steps S101 to S106 are omitted.

On the other hand, if CT imaging is instructed at S101, CT mode is set to the apparatus (S201). Next, it is decided whether offset scan imaging is selected or not (S202). If offset scan is not selected or normal scan is instructed, magnifying factor for CT imaging is set (S203), and a slit for CT scan is selected, the orbit of X-ray beam for normal CT imaging is selected, the rotary arm 30 is positioned relative to the object for positioning the object (S204). Then, normal CT imaging is performed with the imaging conditions set as explained above (S205), wherein the center of the revolution is fixed at the center of the CT imaging region in a plane crossing the rotary shaft, and the supporter is rotated. Next, a CT image is reconstructed based on the acquired projection data (S206), and the obtained CT image is displayed (S207).

On the other hand, if offset scan imaging is selected for CT imaging (NO at S202), magnifying factor is set to the apparatus (S301), and a slit for CT imaging is selected, the orbit of X-ray beam for offset CT imaging is selected, the rotary arm is positioned relative to the object (S302). If necessary, a step for selecting a slit is added, and a slit is selected according to the selection. Then, offset CT imaging is performed with the imaging conditions set as explained above (S303), wherein necessary imaging conditions are set according to the selected imaging configuration. The rotation of the supporter and the two-dimensional relative movement of the rotary shaft by the movement mechanism are performed simultaneously. Next, a CT image is reconstructed based on the acquired projection data (S304), and the obtained CT image is displayed (S305).

In the above-mentioned embodiments, the magnifying factor can be changed. However, needless to say, X-ray CT imaging can be performed even when the magnifying factor is fixed, by displacing the rotary shaft 32 of the rotary mechanism from the revolution center (x) of imaging region and by simultaneously driving the rotation of the rotary arm 30 and the movement of the rotary shaft 32 and/or the imaging region 51. Then, according to the synthesized motion, the center of the imaging region 51 of an object can always be set to the revolution center (x) of imaging region on imaging different from the rotary shaft of the rotation mechanism.

The rotary arm does not necessarily support the X-ray generator and the X-ray detector extending vertically above patient's head. As shown in an example shown in JP-A 2007-143948, the rotary arm may be positioned below a patient, and the X-ray generator and the X-ray detector may be attached to supports extending upward from the lower side.

The rotary shaft 32 is arranged vertically in the embodiment. However, it may be arranged in a horizontal direction as a so-called C-arm, and, for example, a patient lying on his or her back is imaged. In this case, the X-Y table moves the rotary shaft in a plane extending vertically.

The invention can be applied not only to an X-ray CT imaging apparatus for dentistry, but also generally to an X-ray CT apparatus for imaging an object with a relatively small imaging region, such as an X-ray CT apparatus for otolaryngology.

The invention claimed is:

1. An X-ray CT imaging apparatus comprising:
    a first supporter for supporting an X-ray generator generating an X-ray cone beam and a two-dimensional X-ray detector, the X-ray generator and the X-ray detector being arranged to interpose an object, the X-ray detector being adapted to generate a data of an image of the object to be processed for calculating a three dimensional CT data of the object;
    a rotary shaft extending vertically for rotating the first supporter around the rotary shaft to revolve the X-ray generator and the X-ray detector around the object;
    a second supporter supporting the rotary shaft;
    a movement mechanism for moving the first supporter relative to the object; and
    a plane movement mechanism for moving the rotary shaft relative to the object in the movement mechanism;
    wherein in an offset scan CT imaging the revolution of the first supporter around the rotary shaft is performed at the same time as a relative two-dimensional movement of the rotary shaft by the plane movement mechanism; and
    wherein in the relative two-dimensional movement of the rotary shaft, a position of the rotary shaft is moved according to a rotary angle of the first supporter in two dimensions in a plane crossing the rotary shaft along a circular orbit around a center of a CT imaging region, the rotary angle of the first supporter being 360 degrees or more.

2. The X-ray CT imaging apparatus according to claim 1, wherein in the relative two-dimensional movement of the rotary shaft in the offset scan CT imaging, a center of revolution of the X-ray cone beam around the object according to the rotation of the first supporter is set to a position different from a symmetrical axis of the broadening X-ray cone beam.

3. The X-ray CT imaging apparatus according to claim 1, further comprising a mode changer for changing between normal CT imaging mode and offset CT imaging mode;
   wherein in the normal CT imaging mode, the position of the rotary shaft is fixed at a center of a CT imaging region to be imaged in the plane crossing the rotary shaft, and the first supporter is revolved, and
   wherein in the offset CT imaging mode, said offset scan CT imaging is executed.

4. The X-ray CT imaging apparatus according to claim 1, wherein the circular orbit is a true circle.

5. The X-ray CT imaging apparatus according to claim 1, wherein the movement mechanism is set in the second supporter.

6. The X-ray CT imaging apparatus according to claim 1, further comprising an object holder for holding the object, wherein the movement mechanism is set in the object holder.

7. The X-ray CT imaging apparatus according to claim 6, wherein a first part of the movement mechanism for moving the position of the rotary shaft along a first direction in the plane crossing the rotary shaft is set in the second supporter, and a second part of the movement mechanism for moving the position of the rotary shaft in a second direction different from the first direction is set in the object holder.

8. The X-ray CT imaging apparatus according to claim 1, further comprising a device for restricting an irradiation field, wherein the device restricts the X-ray beam generated by the X-ray generator to a narrow width beam having a width narrower in a direction crossing an axial direction of the rotary shaft than in a direction in parallel to the axial direction, and at least one of panorama imaging and cephalometric X-ray imaging is possible by irradiating the narrow width beam.

\* \* \* \* \*